US 11,058,449 B2

(12) United States Patent
Beaupre

(10) Patent No.: US 11,058,449 B2
(45) Date of Patent: Jul. 13, 2021

(54) CURVED ULTRASONIC SURGICAL BLADE

(71) Applicant: Jean Beaupre, Alexandria, KY (US)

(72) Inventor: Jean Beaupre, Alexandria, KY (US)

(73) Assignee: REACH SURGICAL, INC., Tianjin (CN)

( * ) Notice: Subject to any disclaimer, the term of this patent is extended or adjusted under 35 U.S.C. 154(b) by 350 days.

(21) Appl. No.: 15/751,587

(22) PCT Filed: Aug. 12, 2016

(86) PCT No.: PCT/US2016/046911
§ 371 (c)(1),
(2) Date: Feb. 9, 2018

(87) PCT Pub. No.: WO2017/027853
PCT Pub. Date: Feb. 16, 2017

(65) Prior Publication Data
US 2018/0242997 A1 Aug. 30, 2018

Related U.S. Application Data

(60) Provisional application No. 62/204,079, filed on Aug. 12, 2015.

(51) Int. Cl.
*A61B 17/32* (2006.01)
(52) U.S. Cl.
CPC ............ *A61B 17/320092* (2013.01); *A61B 2017/320069* (2017.08); *A61B 2017/320074* (2017.08);
(Continued)
(58) Field of Classification Search
CPC ....... A61B 2017/320074; A61B 2017/320075; A61B 2017/320077; A61B 2017/320096;
(Continued)

(56) References Cited

U.S. PATENT DOCUMENTS

| 2,874,470 A | 5/1954 | Richards |
| 2,984,241 A | 5/1961 | Carlson |

(Continued)

FOREIGN PATENT DOCUMENTS

| GB | 830142 A | 3/1960 |
| GB | 2365775 A | 2/2002 |

(Continued)

OTHER PUBLICATIONS

Office Action from corresponding European Application No. 16836013.9 dated May 10, 2019.

(Continued)

*Primary Examiner* — Shaun L David
(74) *Attorney, Agent, or Firm* — Porter Wright Morrris & Arthur LLP

(57) ABSTRACT

An ultrasonic surgical device including an elongate waveguide having a longitudinal axis and a distal end, and a blade extending away from the distal end of the waveguide, the blade including a curved portion that has at least five faces extending lengthwise along at least a portion of the length of the blade. Each of the faces has a width that extends perpendicular to the longitudinal axis of the waveguide and a length that extends orthogonal to the width. Each of the faces is flat across its width and is either flat along its entire length or includes one or more curved segments along its length, with each of the curved segments of an individual face being curved in the same direction. A method of fabricating an ultrasonic surgical device is also provided.

27 Claims, 19 Drawing Sheets

(52) U.S. Cl.
CPC ............ *A61B 2017/320089* (2017.08); *A61B 2017/320093* (2017.08); *A61B 2017/320094* (2017.08); *A61B 2017/320095* (2017.08)

(58) Field of Classification Search
CPC ........... A61B 2017/320094; A61B 17/320092; A61B 17/320068; B23C 2220/00–68
See application file for complete search history.

(56) References Cited

U.S. PATENT DOCUMENTS

| | | | |
|---|---|---|---|
| 2,990,616 A | 7/1961 | Balamuth et al. | |
| 3,703,037 A | 11/1972 | Robinson | |
| 3,930,173 A | 12/1975 | Banko | |
| 4,283,174 A | 8/1981 | Sertich | |
| 4,283,175 A | 8/1981 | Nash | |
| 4,731,019 A | 3/1988 | Martin | |
| 5,188,102 A | 2/1993 | Idemoto et al. | |
| D339,419 S | 9/1993 | Hood et al. | |
| 5,263,957 A | 11/1993 | Davison et al. | |
| D344,801 S | 3/1994 | Hughes et al. | |
| 5,318,570 A | 6/1994 | Hood et al. | |
| 5,322,055 A | 6/1994 | Davison et al. | |
| 5,531,597 A | 7/1996 | Foulkes et al. | |
| 5,567,153 A | 10/1996 | Foulkes et al. | |
| 5,688,235 A | 11/1997 | Sakurai et al. | |
| 5,746,756 A | 5/1998 | Bromfield et al. | |
| 5,897,523 A | 4/1999 | Wright et al. | |
| 6,024,750 A | 2/2000 | Mastri et al. | |
| 6,206,844 B1 | 3/2001 | Reichel et al. | |
| 6,280,407 B1 | 8/2001 | Manna et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,328,751 B1 | 12/2001 | Beaupre | |
| 6,423,082 B1 | 7/2002 | Houser et al. | |
| 6,660,017 B2 | 12/2003 | Beaupre | |
| 6,752,815 B2 | 6/2004 | Beaupre | |
| 7,479,148 B2 | 1/2009 | Beaupre | |
| 7,799,045 B2 | 9/2010 | Masuda | |
| 8,016,843 B2 | 9/2011 | Escaf | |
| 8,057,498 B2 | 11/2011 | Robertson | |
| 8,147,488 B2 | 4/2012 | Masuda | |
| 8,257,377 B2 | 9/2012 | Wiener et al. | |
| 8,273,087 B2 | 9/2012 | Kimura et al. | |
| 8,323,302 B2 | 12/2012 | Robertson et al. | |
| 8,328,834 B2 | 12/2012 | Isaacs et al. | |
| 8,348,880 B2 | 1/2013 | Messerly et al. | |
| 8,348,967 B2 | 1/2013 | Stulen | |
| 8,430,898 B2 | 4/2013 | Wiener et al. | |
| 8,469,981 B2 | 6/2013 | Robertson et al. | |
| 8,469,982 B2 | 6/2013 | Witt et al. | |
| 8,518,067 B2 | 8/2013 | Masuda et al. | |
| 8,531,064 B2 | 9/2013 | Robertson et al. | |
| 8,540,742 B2 | 9/2013 | Houser et al. | |
| 8,579,928 B2 | 11/2013 | Robertson et al. | |
| 8,668,710 B2 | 3/2014 | Slipszenko et al. | |
| 8,734,476 B2 | 5/2014 | Rhee et al. | |
| 8,911,460 B2 | 12/2014 | Neurohr et al. | |
| 8,951,272 B2 | 2/2015 | Robertson et al. | |
| 8,998,939 B2 | 4/2015 | Price et al. | |
| 9,066,747 B2 | 6/2015 | Robertson | |
| 2004/0077976 A1 | 4/2004 | Wilson | |
| 2006/0100616 A1 | 5/2006 | Beaupre | |
| 2006/0211943 A1 | 9/2006 | Beaupre | |
| 2007/0016236 A1 | 1/2007 | Beaupre | |
| 2007/0043297 A1 | 2/2007 | Miyazawa | |
| 2007/0191713 A1 | 8/2007 | Eichmann et al. | |
| 2007/0198005 A1 | 8/2007 | Ichihashi et al. | |
| 2009/0030439 A1 | 1/2009 | Stulen | |
| 2009/0143806 A1 | 6/2009 | Witt et al. | |
| 2009/0270891 A1 | 10/2009 | Beaupre | |
| 2010/0057118 A1 | 3/2010 | Dietz et al. | |
| 2012/0203143 A1* | 8/2012 | Sanai ............ A61B 17/320092 601/3 |
| 2013/0116717 A1 | 5/2013 | Balek et al. | |
| 2013/0238004 A1 | 9/2013 | Young et al. | |
| 2013/0253559 A1 | 9/2013 | Slipszenko et al. | |
| 2013/0324998 A1 | 12/2013 | Kimball et al. | |
| 2014/0031809 A1* | 1/2014 | Takabayashi .......... A61B 18/18 606/33 |
| 2014/0066962 A1 | 3/2014 | Robertson et al. | |
| 2014/0107537 A1 | 4/2014 | Beaupre | |
| 2014/0163595 A1 | 6/2014 | Witt et al. | |
| 2014/0207163 A1 | 7/2014 | Eichmann et al. | |
| 2014/0358043 A1 | 12/2014 | Akagane | |
| 2015/0164538 A1 | 6/2015 | Aldridge et al. | |
| 2015/0282834 A1 | 10/2015 | Robertson | |
| 2016/0058465 A1 | 3/2016 | Akagane | |
| 2016/0242806 A1 | 8/2016 | Akagane | |
| 2016/0367281 A1 | 12/2016 | Gee et al. | |

FOREIGN PATENT DOCUMENTS

| | | |
|---|---|---|
| WO | 01/24713 A1 | 4/2001 |
| WO | 2015/073428 A1 | 5/2015 |

OTHER PUBLICATIONS

Supplementary European Search Report from corresponding European Application No. 16836013.9 dated Jul. 31, 2018.
Ultracision Incorporated, Harmonic Scalpel Operating Manual, pp. 1-53; Mar. 1995.

\* cited by examiner

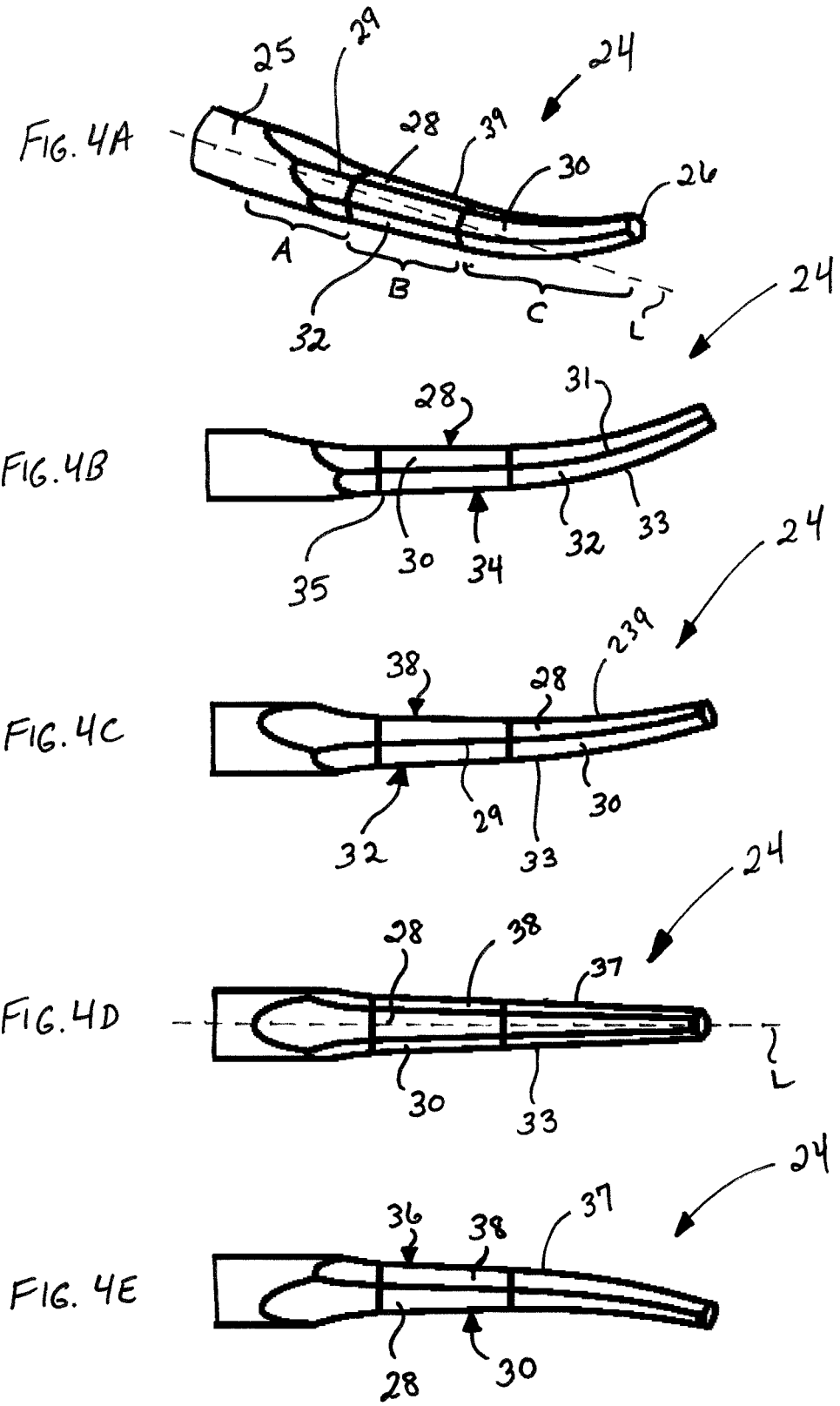

CURVED ULTRASONIC SURGICAL BLADE

CROSS REFERENCE TO RELATED APPLICATIONS

This application claims priority to U.S. Provisional Patent Application No. 62/204,079, filed on Aug. 12, 2015, entitled "Curved Ultrasonic Surgical Blade." The entire disclosure of the foregoing provisional patent application is incorporated by reference herein.

BACKGROUND

Ultrasonically driven surgical blades have been used for quite some time in the cutting, coagulation and/or dissection of tissue during various medical procedures. Compared to conventional static scalpels, for example, ultrasonically driven blades typically require less force for cutting tissue, and can also provide coagulation of blood vessels (particularly when the device includes a clamp member associated with the blade).

Ultrasonic surgical blades are usually provided at the end of an elongate waveguide, which in turn is operatively coupled to an ultrasonic transducer. The transducer, often provided as part of, or housed within, a handpiece, is adapted to convert electrical energy (typically supplied by an external generator) into vibrational motion, typically longitudinal vibrations, at an ultrasonic frequency. In many instances, the transducer includes a "Langevin stack" of piezoelectric disks for this purpose. The standing wave produced by the transducer is transmitted from the transducer to the waveguide, and propagates the length of the waveguide to the blade located at the distal end of the waveguide. As a result, the blade vibrates at an ultrasonic frequency.

When the ultrasonically vibrating blade is urged against tissue, such as by manipulation of a handpiece and/or by clamping tissue between the blade and a clamp member, the mechanical vibratory energy of the blade is transmitted to the tissue, not only cutting the tissue but also generating frictional heat and causing cavitation, coaptation and coagulation of the tissue.

In some instances, the blade is straight and, when used with a longitudinally vibrating transducer, vibrates solely in the longitudinal direction (parallel to the longitudinal axis of the waveguide). However, it is often desirable to provide ultrasonically driven blades that are curved in one or more directions. Curved blades provide a variety of advantages, including greater access to certain sites within a patient as well as improved visibility during use. While curved blades, when operatively connected to a longitudinally vibrating transducer (e.g., via an elongate waveguide) will generally vibrate in at least one non-longitudinal direction (e.g., transversely) due to the asymmetrical nature of the curved blade with respect to the longitudinal axis of the waveguide, such non-longitudinal vibrations in the blade during use can be advantageous. For example, some curved blades that vibrate in at least one non-longitudinal direction may provide greater blade displacement, particularly at the distal end of the blade.

Curved blades, however, can be difficult to manufacture. For example, curved blades of the prior art typically have one or more faces (i.e., surfaces) which are curved in two or more directions, thus requiring the use of specialized equipment such as angled chamfer end mills (also referred to as milling cutters), multiple types of end mills and precise depth-of-cut (Z-axis) control of the milling machine in order to obtain precise blade (i.e., "end effector") geometry. While simpler, square cross-section blades are easier to fabricate, allowing the use of less complex machining processes, these blades do not provide the benefits of a curved blade geometry.

While a variety of devices and techniques may exist for providing curved ultrasonically driven blades, it is believed that no one prior to the inventor has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIG. 4A depicts a perspective view of the blade portion of the ultrasonic surgical device of FIG. 1.

FIGS. 4B-4E depict side views of the blade of FIG. 4A, with each successive view rotated counter-clockwise (as viewed from the distal end of the blade) from the previous view.

Figure 1:
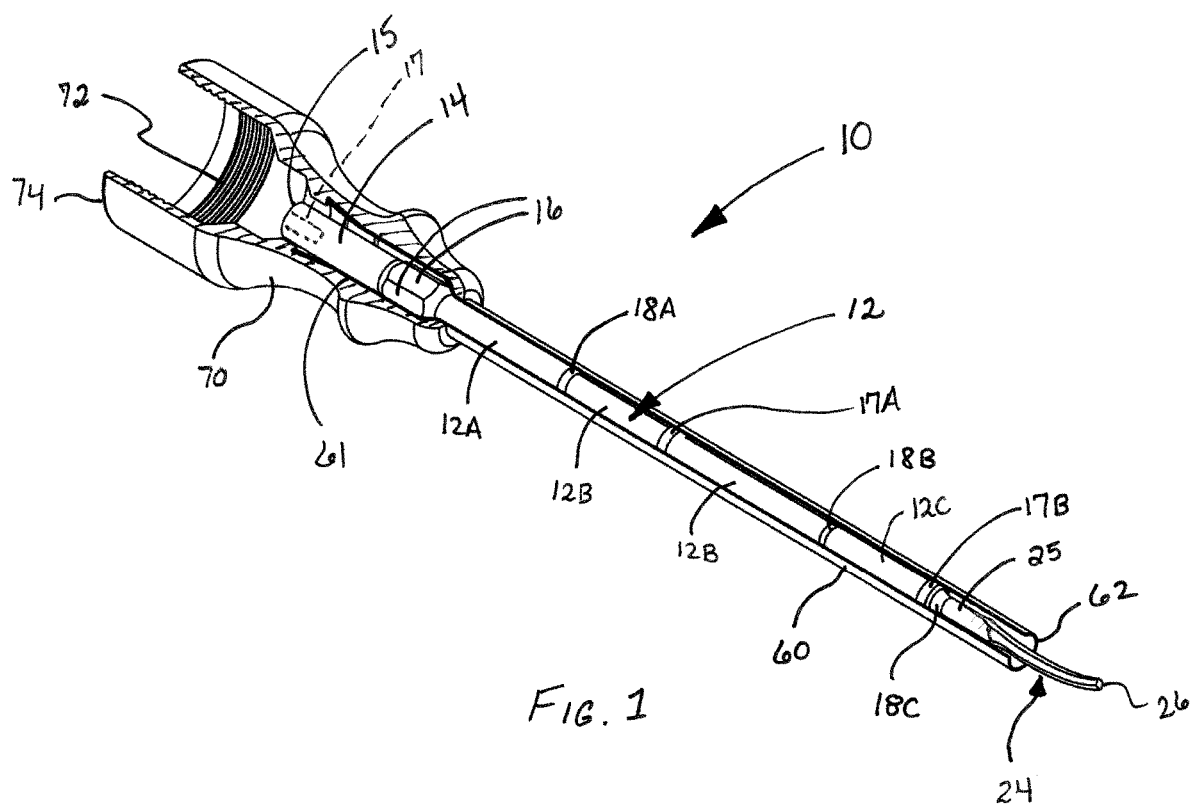
FIG. 1 depicts a partial cross-sectional view of one embodiment of an ultrasonic surgical device having a curved blade.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

Embodiments of the present disclosure provide a curved blade for use with an ultrasonic transducer for medical purposes. The blades described herein have a curved portion that includes at least five faces which extend lengthwise along at least a portion of the blade, at least one of those faces includes one or more curved segments such that the blade has at least one curved surface along with a plurality of blade edges suitable for cutting tissue. Each of the faces of the blade is flat across its width, wherein that width extends perpendicular to the projected longitudinal axis of the waveguide. The curved segments of an individual face are all curved in a single direction, although that curvature may be positive and/or negative on a single face. The curved blade is provided at the distal end of a waveguide, and the waveguide is adapted for operative coupling (directly or indirectly) to an ultrasonic transducer. In some instances, a clamp member is operatively located adjacent to the curved blade for selective engagement with a face and/or an edge of the blade so as to provide for both coagulating and cutting, thus providing a surgical forceps arrangement (also referred to as ultrasonic shears). With or without an associated clamp member, the cutting blade may be used for ultrasonically cutting, coagulating and/or dissecting tissue. It will also be understood that the term "curved segment" encompasses a face having a single curved segment that extends the entire length of that face (e.g., the curved segment length is 100% of the face).

The curved blade embodiments described herein are configured so as to simplify fabrication, while still providing a plurality of blade edges suitable for cutting tissue. By providing a plurality of blade edges, embodiments described herein allow surgeons to employ a greater range of techniques and effects. In addition, curved blade embodiments described herein also allow for tissue cutting in more than one direction, often without the surgeon having to reposition the device.

FIG. 1 is a partially cross-sectional view of one embodiment of an ultrasonic surgical device (10) comprising an elongate waveguide (12) and a curved blade (24). In the particular embodiment shown, ultrasonic surgical device (10) also includes a sheath assembly comprising a hollow cylindrical sheath (60) and a sheath coupler (70) at the proximal end of the sheath (60). In other embodiments, the sheath assembly is omitted.

In the embodiment shown in FIG. 1, the waveguide (12) is located within the sheath (60) and sheath coupler (70). However, the sheath assembly is not secured directly to the waveguide (12). Instead, and as detailed below, waveguide (12) is operatively attachable at its proximal end to an ultrasonic transducer, and sheath coupler (70) is secured to the transducer housing. It will be understood, however, that waveguide (12) may be secured to the sheath assembly (i.e., to sheath (60) and/or sheath coupler (70)), such as by welding, adhesive attachment or in other ways known in the art.

The waveguide (12) includes an internally threaded connector portion (14) at its proximal end, as well as a plurality of flats (16) arrayed about the circumference of the waveguide (12) adjacent to connector portion (14). The flats (16) provide an integral nut on waveguide (12) for use in tightening the waveguide onto a transducer, as explained below. While waveguide (12) is depicted as being of unitary construction, in alternative embodiments waveguide (12) comprises two or more portions joined to one another (e.g., by threaded attachment). For example, in one alternative embodiment, connector portion (14) and flats (16) comprise a unitary structure which is threadably attached at the proximal end of waveguide (12) (e.g., by use of an internally threaded bore and a mating threaded stud connecting the two portions of the waveguide (12)). Similarly, although blade (24) is depicted as being integral with waveguide (12), in alternative embodiments the blade (24) is a separate structure that is attached to the distal end of waveguide (12), such as by threaded attachment.

Figure 2:
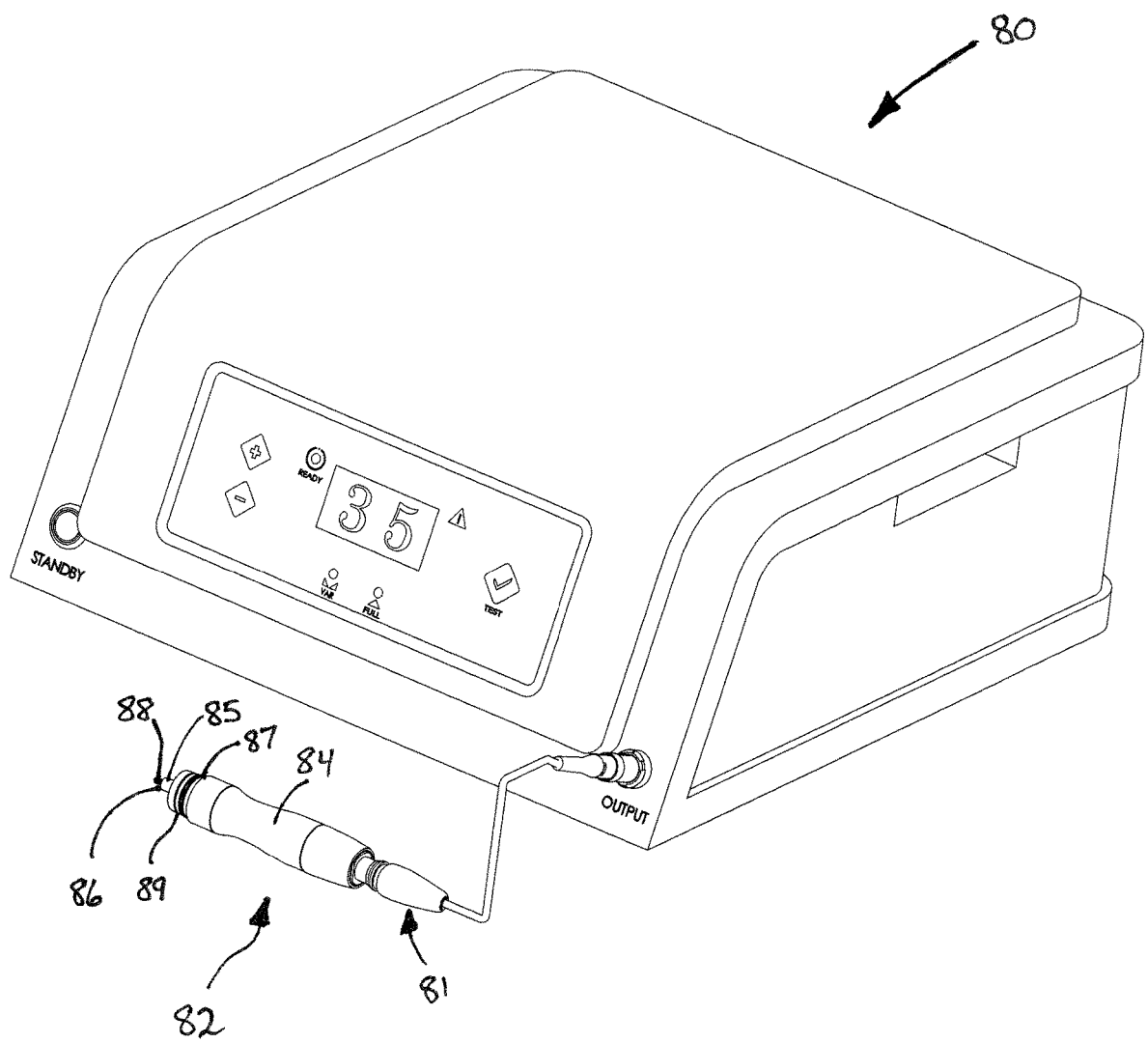
FIG. 2 depicts one embodiment of an ultrasonic generator and attached transducer with which the ultrasonic surgical device of FIG. 1 can be used.

FIG. 2 illustrates an exemplary generator (80) and ultrasonic transducer (82) with which the ultrasonic surgical device (10) may be used. It will be understood that generator (80) and transducer (82) are merely exemplary, as ultrasonic surgical device (10) can be used with any of a variety of generators and transducers. Transducer (82) includes a housing (84) which is configured to facilitate grasping and manipulation of the transducer housing (84) by a medical practitioner. The proximal end of the housing (84) includes an electrical connector (e.g., a plug or a socket) for operative connection to the generator (80) via a mating connector (81) provided at the end of a cable similarly connected to the generator (80). Thus, an electrical drive signal comprising an alternating current of ultrasonic frequency is supplied from the generator (80) to the transducer (82) via the cable and connector (81). Transducer (82) converts the drive signal into a standing, ultrasonic vibrational wave in the transducer, including the distal portion (85) of the transducer horn (or velocity transformer, not shown) which protrudes from the distal end of housing (84). The transducer housing (84) also includes a threaded projection (89) at its distal end, adjacent distal portion (85) of the transducer horn.

A threaded mounting stud (88) is secured to the distal portion (85) of the transducer horn, such as by being threadably and adhesively secured within a threaded bore (not shown) in distal portion (85). Thus, threaded stud (88) extends distally away from the distal end wall (86) of distal portion (85). It should also be pointed out that the distal end wall (86) of distal portion (85) of the transducer horn is located at an antinode of the standing vibrational wave produced by the transducer (82). By way of example, generator (80) and transducer (82) in the depicted embodiment are configured to generate a standing vibrational wave having a frequency of about 55 kHz. However, various other ultrasonic frequencies may be employed, such as between about 20 and about 120 kHz.

Ultrasonic surgical device (10) may be operatively coupled to the transducer (82) in a variety of ways. In the embodiment shown, connector portion (14) at the proximal end of the waveguide (12) includes a threaded bore (17) that extends inwardly (i.e., distally) from the proximal end wall (15) of connector portion (14). Threaded bore (17) is sized and configured to threadably receive mounting stud (88) of transducer (82) therein for operatively coupling the waveguide (12) to the transducer (82). When connector portion (14) is threaded onto the mounting stud (88) of the transducer (82), the proximal end wall (15) of connector portion (14) is in abutment with the distal end wall (86) of distal portion (85) of transducer (82). When coupled in this manner, the standing vibrational wave produced in the transducer is propagated along the length of the waveguide (12). Flats (16) are used to further tighten the waveguide (12) onto the distal end of the transducer (82), and a torque wrench (not shown) may be used to ensure that the waveguide is not over tightened.

As mentioned previously, the sheath assembly comprises cylindrical sheath (60) and sheath coupler (70), which are affixed to one another as shown. The sheath (60) may be affixed to the sheath coupler (70) in a variety of ways such as by welding, adhesive and/or swaging. In the exemplary embodiment shown in FIG. 1, a proximal portion (61) of sheath (60) is secured within a suitably configured cavity within coupler (70), adjacent the distal end of the coupler. In addition, the inner diameter of proximal portion (61) of sheath (60) is larger than the inner diameter of the portion of sheath (60) external to the coupler (70) in order to receive the connector portion (14) and flats (16) of waveguide (12) within proximal portion (61).

Sheath coupler (70) is generally hollow and includes a threaded cavity (72) extending inwardly away from proximal end wall (74) of the coupler (70). Once the waveguide (12) has been operatively coupled to the transducer (82) in the manner described previously, the sheath assembly is slid over the waveguide (12). In particular, blade (24) is inserted through the threaded cavity (72) followed by waveguide (12). Thereafter, sheath coupler (70) is threadably secured to the transducer housing (84) by the threaded engagement of threaded projection (89) within threaded cavity (72), with the proximal end wall (74) of the coupler (70) in abutment with the end wall (87) of transducer housing (84). Once assembled in this manner, at least a portion of blade (24) extends beyond the distal end wall (62) of sheath (60), as seen in FIG. 1. In other words, in some embodiments, a proximal portion of the blade (including proximal portions of the faces of the blade, described further herein) is positioned within the sheath, while a distal portion of the blade extends beyond the distal end wall of the sheath (as depicted in FIG. 1). Of course, it will be understood that the waveguide (12), blade (24), and/or sheath assembly can be configured such that either more or less of the blade (24) extends beyond the distal end (62) of sheath (60) than is depicted in FIG. 1 (see, e.g., FIGS. 3A and 3B). In general, enough of blade (24) should protrude beyond the distal end of sheath (60) to provide adequate visualization, reach, and manipulation of the blade for cutting, dissection and coagulation during use, while not having so much of the blade (24) exposed that there is a heightened risk of unintended contact between the blade (24) and tissue.

In the embodiment shown in FIG. 1, between about 0.5 and about 2.5 cm of blade (24) extends beyond the distal end wall (62) of sheath (60). In other embodiments, between about 1.0 and about 2.0 cm of blade (24) extends beyond the distal end wall (62) of sheath (60). In still further embodiments, about 15% to about 85% of the distal ¼ wave, or about 30% to about 70% of the distal ¼ wave of the blade (24) is exposed. The distal ¼ wave is the region extending between the most distal vibrational node and the distal tip (26) of the blade—i.e., approximately the length of the blade (24) which extends from approximately the most distal node to the distal tip (26).

During use of the ultrasonic surgical devices and blades described herein, various forces applied at the blade (24) will tend to cause lateral deflection of the waveguide (12) within the sheath (60). In order to prevent contact between the inner wall of sheath (60) and blade (24) and waveguide (12), thereby limiting or preventing potential damage to the ultrasonic device (10) as well as damping of the standing wave, one or more spacers are provided between the waveguide (12) and the interior of sheath (60) in order to maintain the waveguide (12) in the center of the sheath (60) (i.e., the longitudinal axis of the waveguide (12) aligned with the longitudinal axis of the sheath (60)). In the embodiment shown in FIG. 1, resilient rings (17A, 17B) are provided on the exterior of waveguide (12), and comprise, for example, silicone rings. Since the amplitude of the longitudinal vibration of the waveguide (12) at the driving frequency (e.g., 55 kHz) during use is zero at the nodes of the standing wave, the resilient rings (17A, 17B) are located at or near the vibrational nodes of the waveguide (12) in order to limit damping of the standing wave. Rings (17A, 17B) also damp any vibrations having frequencies other than the drive frequency, since the nodes of vibrations of other frequencies will generally not coincide with the node locations for the drive frequency.

Figure 18:
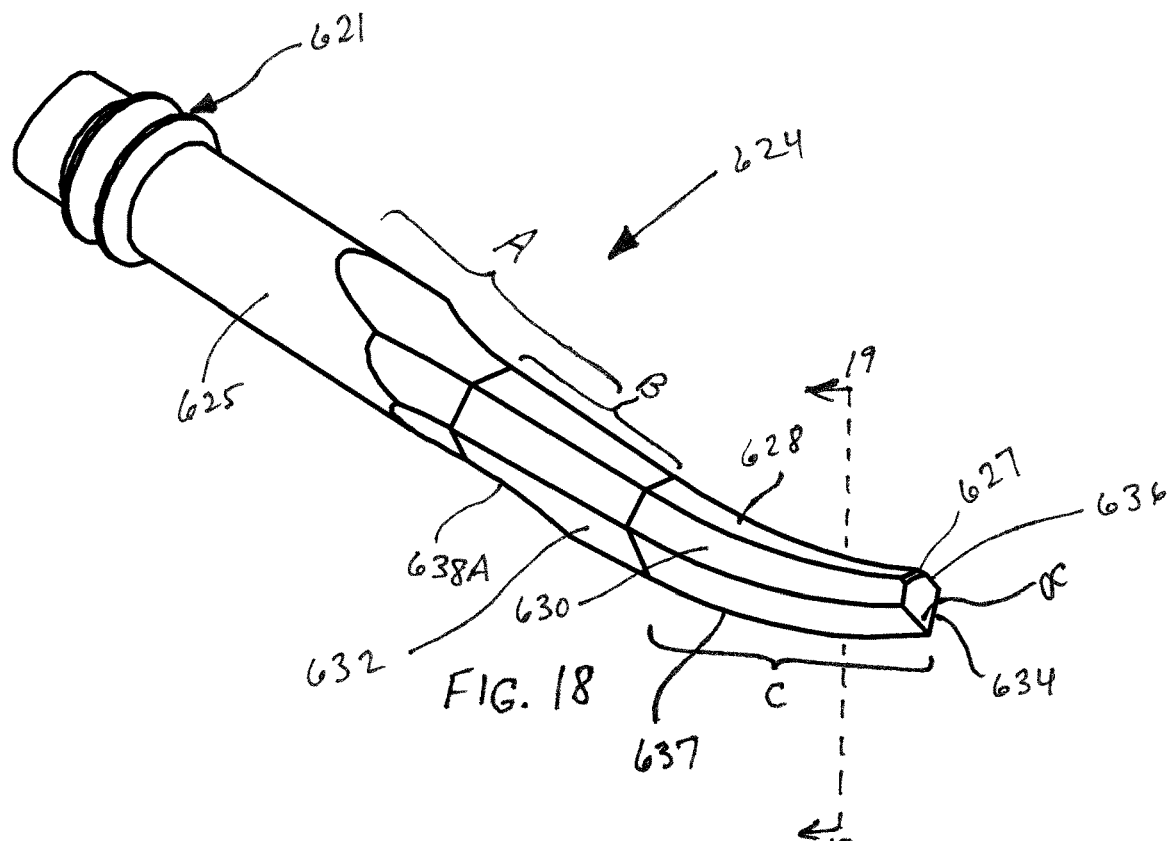
FIGS. 18 and 19 depict perspective, and partially cutaway perspective views of another alternative blade.
Figure 19:
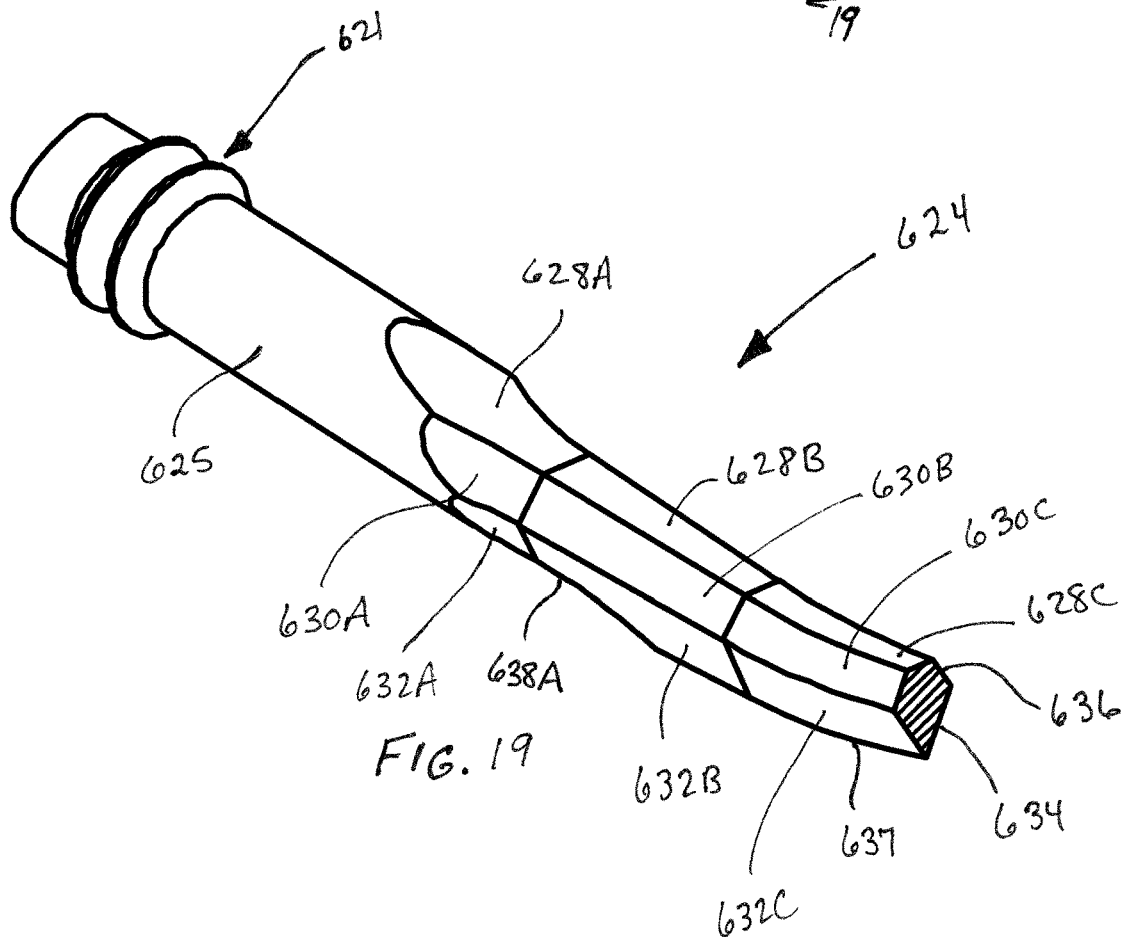

Resilient rings (17A, 17B) can be supported and maintained in place in a variety of ways known to those skilled in the art. For example, in the embodiments shown in FIGS. 6, 7 and 14, an annular support (220, 320, 420) for a resilient ring is provided on the waveguide, and the resilient ring can be, for example, insert molded over the support (220, 320, 420) or secured over the annular support in other ways known to those skilled in the art (e.g., adhesively, bonding, etc.). Annular supports can be formed, for example, by lathe turning. As yet another alternative, and as seen in the embodiment of FIGS. 18 and 19, a circumferential groove (621) is provided on the waveguide (e.g., by lathe turning so as to form two adjacent rings with the groove located therebetween). The resilient ring can then be maintained in position mechanically by trapping the ring within groove (621). Similar arrangements may be employed for securing additional resilient rings about the waveguide. In some embodiments, resilient rings (17A, 17B) are provided at or near two or more vibrational nodes, depending in part on the length of the waveguide.

As is known to those skilled in the art, a variety of other features may be provided on the waveguide (12). For example, waveguide (12) shown in FIG. 1 includes a plurality of segments of varying diameter, with tapers (18A, 18B, 18C) providing a smooth transition between segments of different diameters. In the exemplary embodiment shown in FIG. 1, first segment (12A) is located adjacent flats (16) and has a diameter smaller than that of the flats (16) region in order to amplify the standing vibrational wave. A first taper (18A) is located at the distal end of first segment (12A), and provides a smooth transition from the larger diameter of first segment (12A) to the smaller diameter of second segment (12B). Similarly, a second taper (18B) is located at the distal end of second segment (12B), and provides a smooth transition from the smaller diameter of second segment (12B) to the larger diameter of third segment (12C). Finally, a third taper (18C) is located at the distal end of third segment (12C) (adjacent resilient ring (17B), at the most-distal vibrational node of the waveguide), and provides a smooth transition from the larger diameter of third segment (12C) of waveguide (12) to the smaller diameter of the blade (24). These changes in diameter serve to, among other things, adjust the amplitude and/or frequency of the vibrational wave propagating the length of the waveguide. It will be understood, however, that this is merely one exemplary arrangement of the waveguide. Alternative embodiments include any number of segments of varying diameters, depending, in part, on the desired length of the waveguide (which will depend, for example, on the intended use of the instrument).

The ultrasonic surgical device comprising waveguide (12) and blade (24) can be made from any of a variety of materials, particularly various medically and surgically acceptable metals such as titanium, titanium alloy (e.g., Ti6Al4V), aluminum, aluminum alloy, or stainless steel. The waveguide (12) and blade (24) shown in FIG. 1 are formed as a single unit, fabricated from a single metal rod that has been milled so as to provide the depicted features. Alternately, the waveguide and blade may comprise two or more separable components of the same of differing compositions, with the components coupled to one another by, for example, adhesive, welding, a threaded stud, and/or other suitable ways known to those skilled in the art. For example, waveguide (12) may be configured as two pieces joined together at or between flats (16) and first segment (12A). Similarly, blade (24) may be constructed separately from waveguide (12) and joined to the distal end of waveguide (12).

It will also be understood that the ultrasonic surgical device comprising waveguide (12) and blade (24) may be used without the sheath assembly simply by operatively coupling the proximal end of the waveguide (12) (i.e., connector portion (14)) to transducer (82) (via threaded mounting stud (89)). Sheath (60), however, not only protects the waveguide (12), but also prevents inadvertent contact between the waveguide (12) and the patient, medical personnel or the surgical environment. Not only will such contact damp vibration of the waveguide (12), but it can also cause injury to the patient or medical personnel since the waveguide (12) is ultrasonically vibrating.

Figure 3A:
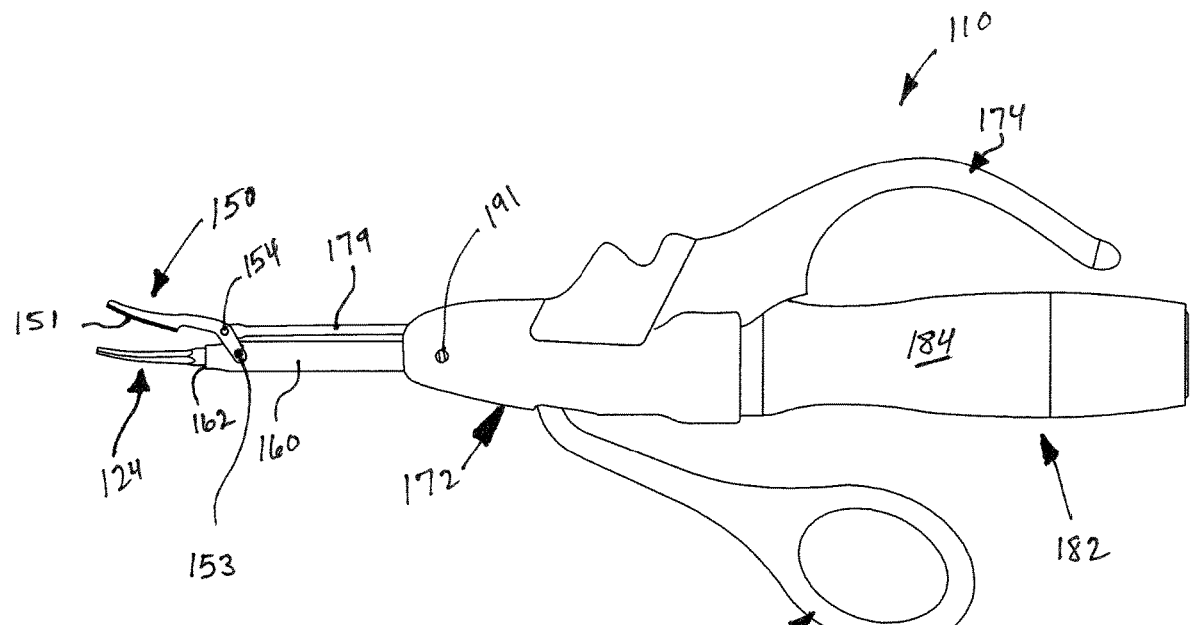
FIG. 3A depicts a schematic side view of an ultrasonic shears device.
Figure 3B:
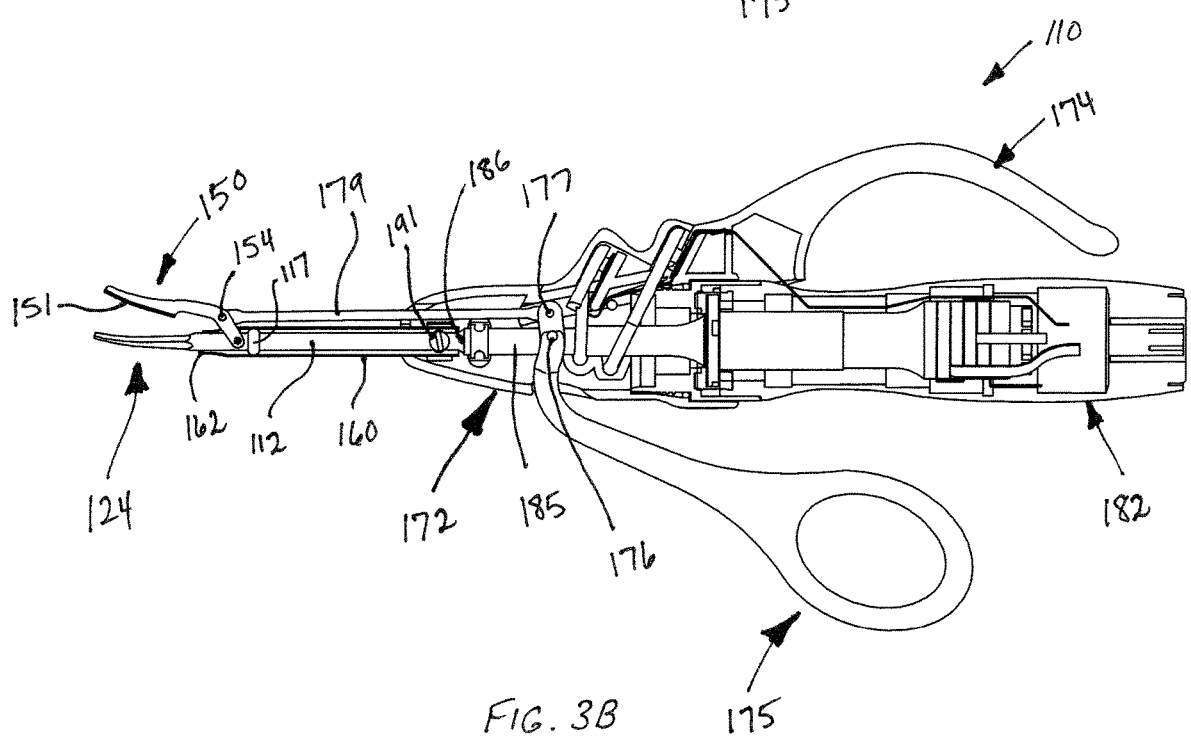
FIG. 3B depicts a partial cross-sectional view of the ultrasonic shears device of FIG. 3A.

An alternative embodiment of an ultrasonic surgical device (110) is depicted in FIGS. 3A and 3B, wherein the device (110) is configured as ultrasonic shears (also known as a clamp coagulator or ultrasonic forceps) having a clamp member (150) pivotally supported adjacent curved blade (124). The clamp member (150) is adapted for selective engagement with a face or an edge of the blade (124) so as to provide for the simultaneous cutting and coagulation of tissue urged against a face or edge of blade (124) by the clamp member (150). Blade (124) is similar to blade (24) in FIG. 1 or may be configured similar to the various other curved blade embodiments described herein. In the embodiment shown, clamp member (150) is located and configured for selective engagement with an upper, concavely curved face of the blade (124).

Ultrasonic surgical device (110) is, apart from the blade (124) and the clamp member (150), similar to the apparatus shown and described in U.S. Pat. No. 5,322,055 (which is incorporated by reference herein). Like the previous embodiment, the curved blade (124) is provided at the distal end of an elongate waveguide (112). While waveguide (112) and blade (124) are depicted as being of unitary construction, in alternative embodiments waveguide (112) comprises two or more portions joined to one another (e.g., by threaded attachment). Similarly, although blade (124) is depicted as being integral with waveguide (112), in alternative embodiments the blade (124) is of separate structure and attached to the distal end of waveguide (112), such as by threaded attachment. Ultrasonic surgical device (110) also includes a hollow cylindrical sheath (160) in which at least a portion of waveguide (112) and optionally a portion of blade (124) is positioned.

As in the previous embodiment, although at least a portion of the waveguide (112) is located within the sheath (160), the sheath (160) is not secured directly to the waveguide (12). Instead, and as detailed below, waveguide (112) is operatively attached at its proximal end to a transducer (182), and the proximal end of sheath (160) is secured within the handpiece (172).

Ultrasonic surgical device (110) further includes an ultrasonic transducer (182) mounted to the handpiece (172), as shown. Transducer (182) may be removably mounted to the handpiece (172), such as by threaded engagement therewith, or may be fixed within or on the handpiece (172). Transducer (182) includes a housing (184) which is configured to facilitate grasping and manipulation of the surgical device (110) along with stationary handle (174) of handpiece (172). The proximal end of the transducer housing (184) includes an electrical connector (e.g., a plug or a socket) for operative connection to a generator. Thus, an electrical drive signal comprising an alternating current of ultrasonic frequency will be supplied from the generator to the transducer (182) via a cable operatively connected to the electrical connector on the transducer housing. As with the previous embodiment, transducer (182) converts the drive signal into a standing, ultrasonic vibrational wave in the transducer, including the transducer horn (or velocity transformer) (185).

Although not shown in FIG. 3A or 3B, a threaded mounting stud is secured to the distal end (186) of the transducer horn (185), such as by being threadably and adhesively secured within a threaded bore in the distal end (186) of the transducer horn (185). Thus, as in the previous embodiment, this threaded stud extends distally away from the distal end (186) of transducer horn (185), and this distal end (186) of transducer horn (185) is located at an antinode of the standing vibrational wave produced by the transducer (182) (e.g., at 55 kHz). Similar to the previous embodiment, the proximal end of waveguide (112) includes a threaded bore (not shown) that extends inwardly (i.e., distally) from the proximal end of the waveguide (112). This threaded bore is sized and configured to threadably receive the mounting stud on the distal end of the transducer horn (185), such that the waveguide (112) is operatively coupled to the transducer (182) by threadably securing the waveguide onto the mounting stud of the transducer horn (185). When coupled in this manner (i.e., as seen in FIG. 3B), the standing vibrational wave produced in the transducer (182) is propagated along the length of the waveguide (112).

The sheath (160) may be affixed to the handpiece (172) in a variety of ways known to those skilled in the art, such as by welding, adhesive, mechanical fasteners and/or swaging. In the exemplary embodiment shown in FIGS. 3A and 3B, the proximal end of sheath (160) and the waveguide (112) are secured within handpiece (172) by a mounting pin (191).

As seen in FIG. 3A, at least a portion of blade (124) extends beyond the distal end wall (162) of sheath (160). Once again it will be understood that the waveguide (112), blade (124), sheath (160) and/or handpiece (172) can be configured such that more or less of the blade extends beyond the distal end of sheath (160) than depicted in FIG. 3A. In this instance, the entirety of the blade faces (i.e., the curved portion of the blade) extends beyond the distal end wall (162) of sheath (160). As with the previously described embodiment, one or more resilient rings (117) are provided on the exterior of waveguide (112) (e.g., silicone rings) and act as spacers that not only maintain the waveguide (112) centered with sheath (160), but also are located at vibrational nodes of the waveguide (112) in order to limit damping of the standing wave at the drive frequency while also damping frequencies other than the drive frequency.

Figure 17:
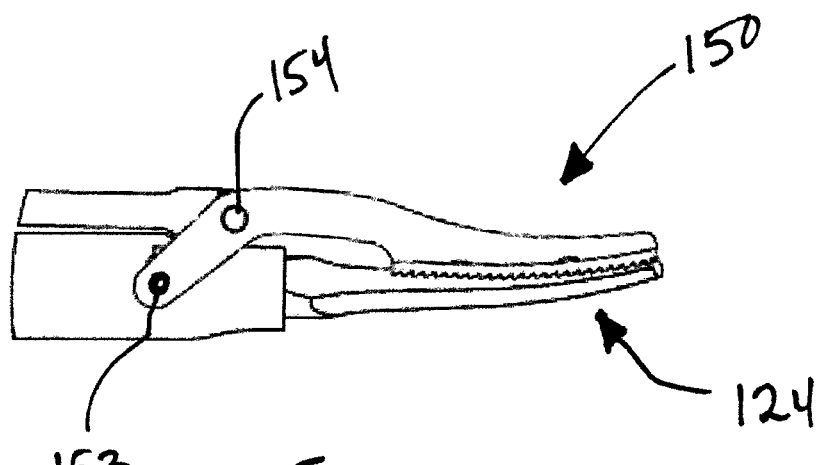

Clamp member (150) includes a pad (151) mounted thereto for compressing tissue against a face or edge of the blade (124) in order to facilitate the cutting and coagulating of tissue. Pad (151) is formed of a polymeric or other compliant material, and engages an edge or face of the blade (124) when the clamp member (150) is pivoted to its fully closed position shown in FIG. 17. Pad (151) can comprise, for example, PTFE or polyimide (PI), with or without added filler materials such as glass, metal and/or carbon. In some embodiments, pad (151) comprises a high temperature resistant material. Pad (151) is attached to the clamp member (150) by, for example, an adhesive or mechanical fastener. As seen in FIGS. 3A and 3B, the exposed surface of the pad (151) provides a curved tissue-engaging surface. In the embodiment shown, this tissue-engaging surface has a curvature corresponding to the curvature of the corresponding portion of the first face of the blade.

Figure 16:
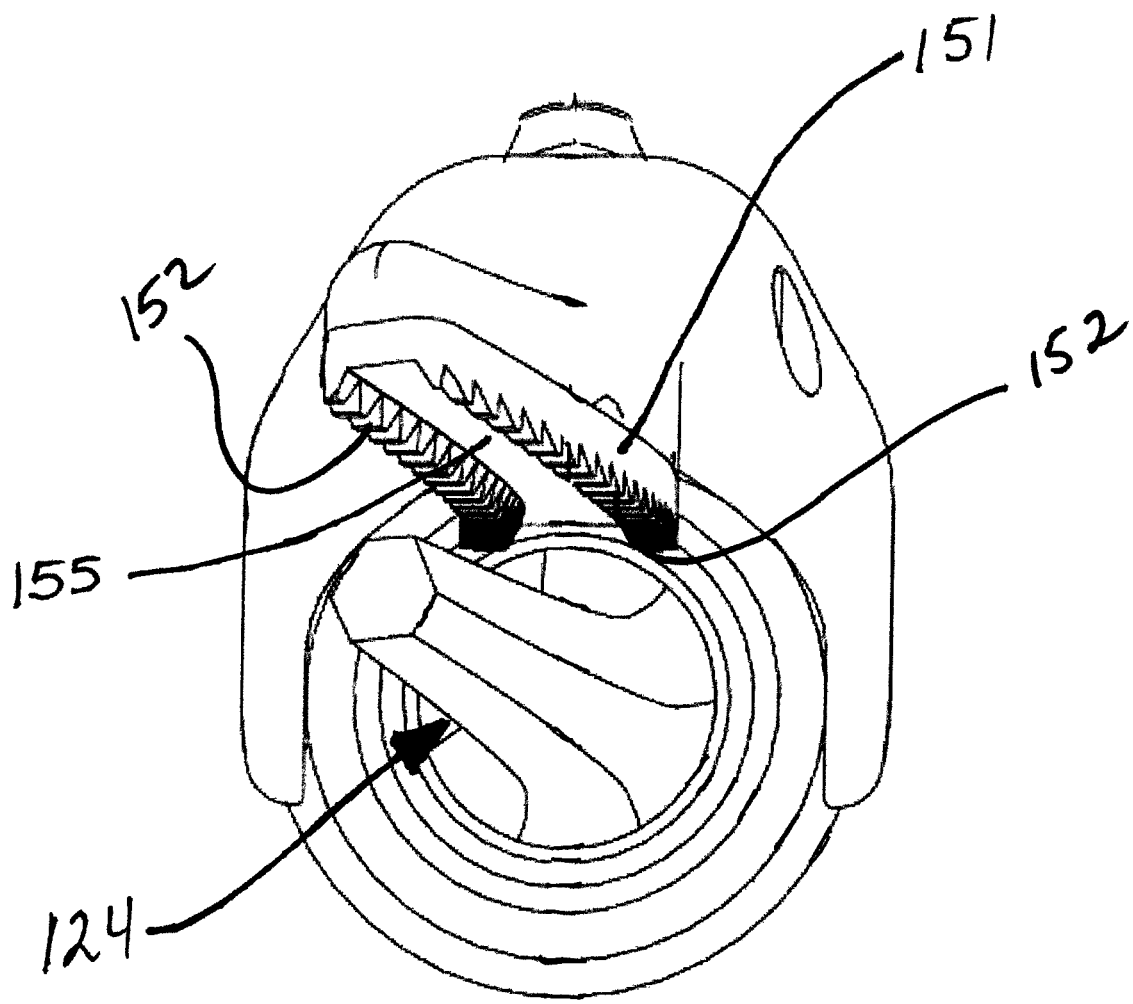
FIGS. 16 and 17 depict front perspective and side views of the distal portion of the ultrasonic shears device of FIGS. 3A and 3B, with FIG. 17 depicting the clamp member in its fully closed position against the blade.

In addition, as best seen in FIG. 16, serrations (152) are formed in the clamping surface of pad (151) in order to enhance tissue grasping and manipulation, even when the blade (124) is not vibrating, thus allowing the surgical device (110) to be used as a conventional forceps when not being used for cutting/coagulating tissue. The serrations (152) are provided in two rows, with a recessed region (152) therebetween. Recessed region (152) is shaped and configured for mating engagement with an adjacent face of the blade (124), as best seen in FIG. 16. By conforming the surface of recessed region (152) to that of the adjacent face of the blade (124), there are no gaps between the tissue pad (151) and the blade when the tissue pad is clamped against the adjacent face of the blade, thus ensuring that tissue is cut completely along the length of the blade. It will also be noted that the distal end of sheath (160) is tapered in order to limit tissue from entering the interior of the sheath (160) during use.

The proximal end of the clamp member (150) is pivotally mounted to the sheath (160), adjacent the distal end thereof, by a pivot pin (153). The clamp member (150) is also pivotally attached to the distal end of an actuator rod (179) at pivot pin (154). Actuator rod (179) is mounted to the handpiece (172) for linear movement parallel to the longitudinal axis of waveguide (112), and extends outwardly from the handpiece (172) directly above the sheath (160). From the open position of FIG. 3A, linear movement of the actuator rod (179) in the distal direction (i.e., towards blade (124)), causes the clamp arm to pivot towards its closed position, such that pad (151) will eventually engage a face of the blade (124) (see FIG. 17). Similarly, from the closed position, linear movement of the actuator rod (179) in the proximal direction (i.e., towards transducer (182)), causes the clamp arm to pivot to its open position of FIG. 3A.

In order to effect linear, longitudinal movement of actuator rod (179), a pivoting handle (175) is pivotally mounted to handpiece (172), as shown. Handle (175) is pivotally secured within handpiece (172) at pivot pin (176), and the distal end of handle (175) is pivotally attached to the proximal end of actuator rod (179) at pivot pin (177) within handpiece (172). Thus pivotal movement of handle (175) away from handpiece (172) causes the clamp member (150) to pivot towards its open position (FIG. 3A), while pivotal movement of handle (175) towards handpiece (172) causes the clamp member (150) to pivot towards its closed, tissue clamping, position.

As mentioned previously, the blades depicted and described herein have at least one curved surface along with a plurality of blade edges suitable for ultrasonic cutting of tissue. These blades can be fabricated from turned stock (e.g., round stock) using only end mills and no Z-axis milling, while still providing a plurality of blade edges suitable for cutting tissue.

The curved blades depicted and described herein are provided at the distal end of a waveguide, and have a curved portion that includes at least five faces that extend lengthwise along at least a portion of the length of the blade. Each of the faces of the blade is flat across its width, which width extends perpendicular to the projected longitudinal axis (L) of the waveguide. Along their respective lengths (i.e., the direction orthogonal to their respective widths), each of the blade faces is either flat or includes one or more curved segments (with or without one or more flat segments), with each of the curved segments of an individual face being curved in the same direction (however, that curvature can be positive and/or negative curvature). At least one of the faces of the blade includes at least one of said curved segments. In some embodiments wherein the curved portion of the blade has an even number of faces (e.g., six), two opposing faces (i.e., faces on opposite sides of the blade) have at least one curved segment. The direction of curvature of the curved segments of an individual face does not change along its length, with the curvature gradient on the surface of the curved segments of each face being non-zero in one direction and zero in the perpendicular direction (i.e., across their widths). Thus, the axes of curvature of each of the curved segments of an individual face are parallel to one another (as seen, for example, in FIG. 5). In addition, the axes of curvature of each of the curved segments of the faces of the blade is perpendicular to a plane which includes the longitudinal axis (L) of the waveguide (i.e., the faces of the blade include no curved segment having an axis of curvature which is not perpendicular to a plane which includes the longitudinal axis of the waveguide). Thus, the included angle between adjacent faces is also constant along the length of the curved portion of the blade.

Accordingly, each of the faces of the curved portion of the blade comprises a developable surface, thereby facilitating the manufacture of the blade from turned stock (e.g., round stock) using an end mill and only X- and Y-axis movement of the workpiece (i.e., the blade material, e.g., round stock) and mill with respect to one another. No Z-axis movement or cutting is required during milling, since each of the faces of blade is flat and/or includes one or more right cylindrical surfaces (circular or elliptic cylindrical surfaces) or other surface that is curved in a single direction. It will be understood that the blades described herein can be fabricated from any turned stock, including not only straight or tapered cylindrical stock but also straight or tapered elliptical turned stock. (The configuration of the blade faces described by the foregoing may be better understood with references to the method of producing the blade faces from round stock, as further described herein.)

The intersection of each pair of adjacent faces of the curved portion of the blade defines a cutting edge, which extends along at least a portion of the length of the blade.

Because each adjacent blade face is not necessarily curved in the same manner, a variety of cutting edge shapes and configurations can be provided on the same blade in order to give more cutting options to the medical practitioner.

In some embodiments, the five or more faces of the blade, and hence the five or more cutting edges therebetween, extend to the distal tip (26) of the blade (e.g., FIG. 6). In other embodiments (e.g., FIG. 15), one or more of the blade faces terminates in a cylindrical face (527) (or other turned surface). Cylindrical face (527) results when two adjacent faces intersect along the length of the blade but adjacent their distal ends that intersection extends outside the turned profile of the stock used to fabricate the blade. In the embodiments shown in FIG. 15, cylindrical face (527) comprises a portion of the cylindrical stock from which blade (524) has been fabricated. It will be understood, however, that the blade described herein can be fabricated from any turned stock, including not only cylindrical stock but also, for example, elliptical turned stock.

In some embodiments, the curved portion of the blade has six faces arranged as three pairs of opposing faces, such that the cross-sectional shape of the blade in any plane perpendicular to the longitudinal axis of the waveguide through the curved portion of the blade (except through some transition segments, as described below) is a hexagon. The included angle between adjacent faces in these embodiments is constant along the length of the curved portion of the blade, and each is between about 100 and about 140 degrees. In one particular embodiment, all of the included angles between adjacent faces of a blade having a curved portion with six faces are about 120 degrees (e.g., blade 424 in FIG. 14).

The proximal end of the blade in some embodiments includes a cylindrical section between the distal end of the waveguide and the plurality of faces of the blade. Blade (24), for example, includes cylindrical portion (25) located between the taper (18C) adjacent the most-distal node of the waveguide (12) and the proximal ends of blade faces (28, 30, 32, 34, 36, 38) (see FIGS. 1 and 4A). In other embodiments, particularly when a taper is not provided at the distal-most node, the blade includes a cylindrical portion located between the distal-most node of the waveguide and the plurality of faces (i.e., when there is no taper between the distal-most node and the blade). In addition, in still further embodiments, no such cylindrical portion is included on the proximal end of the blade.

FIGS. 4A-4E depict various views of blade (24) which, in this embodiment, includes a curved portion having six faces (28-38) extending distally away from cylindrical portion (25) to distal tip (26). In this particular embodiment, each face (28-38) includes a curved transition segment (A), a flat middle segment (B) and a curved distal segment (C). Transition segments (A) of each face provide a smooth transition from cylindrical portion (25) to the middle and distal segments (B, C) of the curved portion of the blade, and gradually increase in width in the distal direction (i.e., towards distal tip (26)). Not only are the transition segments (A) necessitated by the use of an end mill to form the blade faces in turned stock, the transition segments (A) help to reduce stress at the intersection of the faces and the cylindrical portion (25). Nevertheless, the transition segments (A) as well as the edge between a transition segment (A) and the adjacent face (e.g., an adjacent transition segment) are also usable portions of the blade. Thus, each of these transition segment edges can be used for cutting and/or cauterizing tissue.

Transition segment (A) of each of the blade faces is flat across its width and curves in a single direction along its length. In the embodiment shown in FIGS. 4 and 5, middle segment (B) of each of the blade faces, on the other hand, is flat across its width and also flat along its length, extending at an angle to the longitudinal axis of the waveguide such that the blade (24) is tapered along middle segments (B). In alternative embodiments, one or more of the middle segments (B) extend parallel to the longitudinal axis (L) of the waveguide. Finally, each distal segment (C) of each of the faces of blade (24) is flat across its width and curved (in a single direction) along its length. In alternative embodiments, one or more (but not all) of the distal segments (C) are flat along their respective lengths.

As mentioned above, the curved portion of blade (24) has six faces (28-38) extending distally away from cylindrical portion (25) to distal tip (26). The faces of blade (24) are arranged as three pairs of opposing faces, such that the cross-sectional shape of the blade in any plane perpendicular to the longitudinal axis (L) of the waveguide through any point of middle segments (B) or distal segments (C) is a hexagon. The included angle between adjacent faces is constant along the length of the blade, and each is between about 100 and about 140 degrees. In the embodiment shown in FIG. 4, all of the included angles between adjacent faces are about 120 degrees such that the cross-sectional shape of the blade in any plane perpendicular to the longitudinal axis (L) of the waveguide through any point of middle segment (B) or distal segment (C) is an equiangular hexagon.

It should be noted that an equiangular hexagon simply means that the included, i.e., interior, angles are identical, and opposing sides of the hexagon are parallel to one another. However, since the equiangular hexagonal cross-sectional shape described above is defined in a plane perpendicular to the longitudinal axis (L) of the waveguide and opposing faces, although parallel across their widths and only curving in a single direction, may have different amounts of curvature, opposing sides of this equiangular hexagon are not necessarily the same length. Thus, the blades described herein, although capable of being manufactured using only conventional end mills and no Z-axis milling, can have a plurality of curved cutting edges which are not necessarily curved in a single direction (despite the fact that each individual face is curved in only one direction).

Of course it will be understood that the included angle between adjacent faces in alternative embodiments will depend, in part, on how many faces are provided on the blade. For example, in some embodiments of a blade having five faces, each of the included angles between adjacent faces is between about 88 and about 128 degrees, or, in some instances, each is about 108 degrees such that the cross-sectional shape of the blade in any plane perpendicular to the longitudinal axis of the waveguide through the curved portion of the blade (except through some transition segments, where present) is an equiangular pentagon. Similarly, in some embodiments of a blade having seven faces, each of the included angles is between about 108 and about 148 degrees, or, in some instances, each is about 128 degrees such that the cross-sectional shape of the blade in any plane perpendicular to the longitudinal axis of the waveguide through the curved portion of the blade (except through some transition segments, where present) is an equiangular heptagon. And in some embodiments of a blade having eight faces, each of the included angles is between about 115 and about 155 degrees, or, in some instances, each is about 135 degrees such that the cross-sectional shape of the blade in any plane perpendicular to the longitudinal axis of the waveguide through the curved portion of the blade (except through some transition segments, where present) is an equiangular octagon.

In still further embodiments, the blade may be configured to have a greater variation in the included angles than those specified in the previous paragraphs. Thus, at least one of the included angles between adjacent faces is more than 20 degrees, more than 30 degrees, or more than 45 degrees less than at least one of the other included angles along at least a portion of the blade. For example, blade (624) shown in FIGS. 18 and 19 has five faces such that the cross-sectional shape of the blade in any plane perpendicular to the longitudinal axis of the waveguide through the curved distal segments (C) of the blade (624) is a pentagon. However, although four of the included angles between adjacent faces is about 120 degrees, the fifth included angle (α) is about 60 degrees. Thus, cutting edge (637) is sharper than the other four cutting edges.

Figure 5:
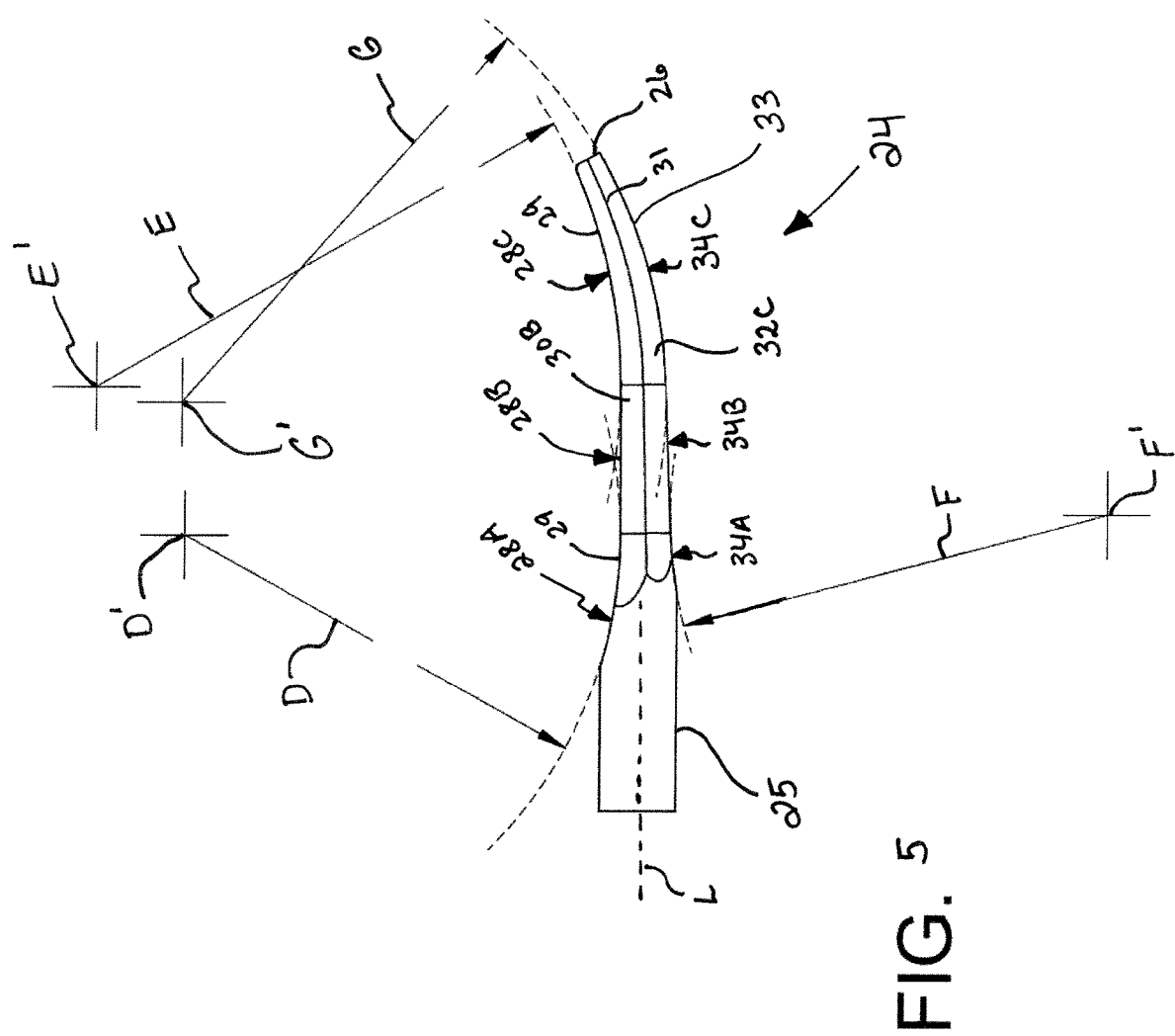
FIG. 5 depicts an enlarged view similar to FIG. 4B.
Figure 6A:
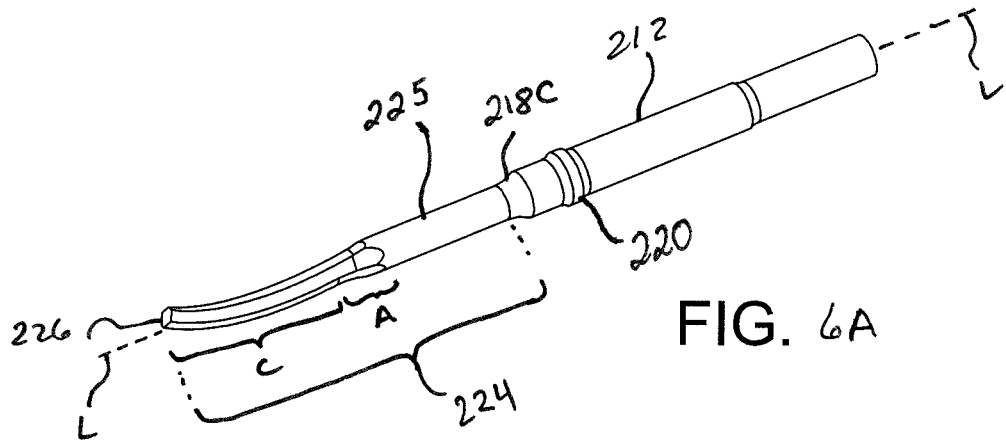
FIGS. 6A-6E depict views similar to FIGS. 4A-4E of an alternative embodiment of a blade, with each successive view rotated clockwise (as viewed from the distal end of the blade) from the previous view.
Figure 6D:
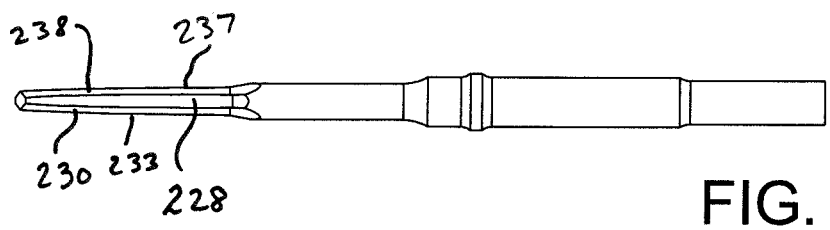
Figure 6B:
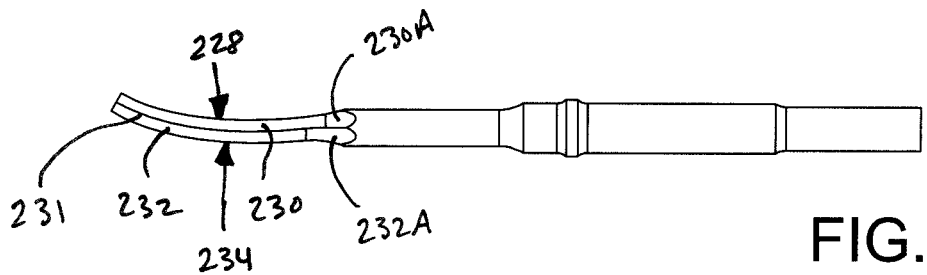
Figure 6C:
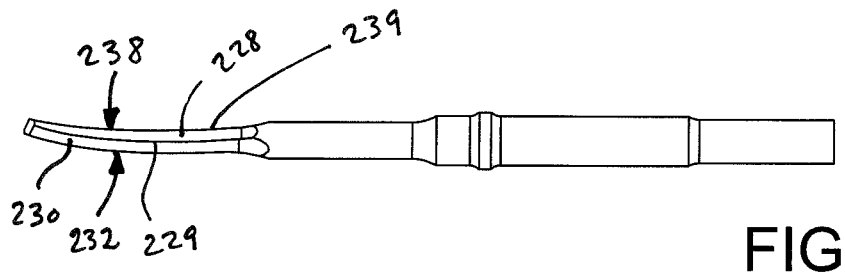
Figure 6E:
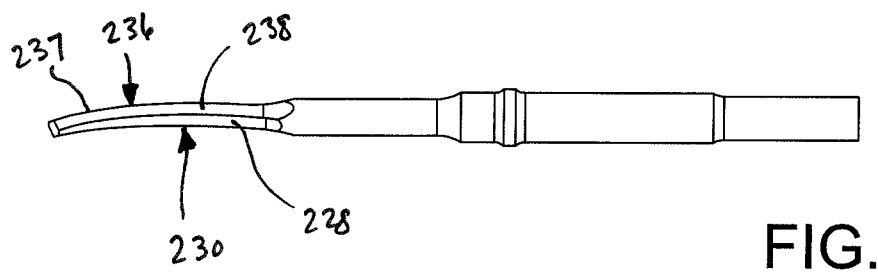
Figure 12B:
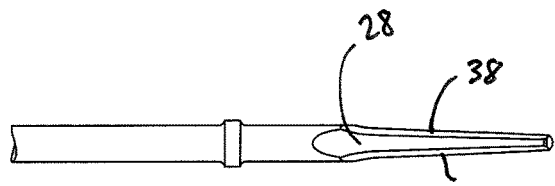
Figure 12D:
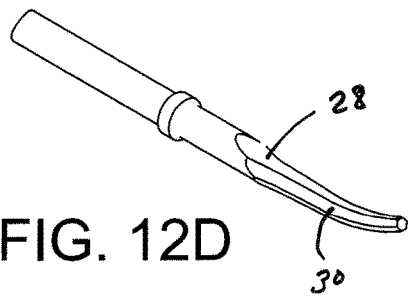
Figure 12A:
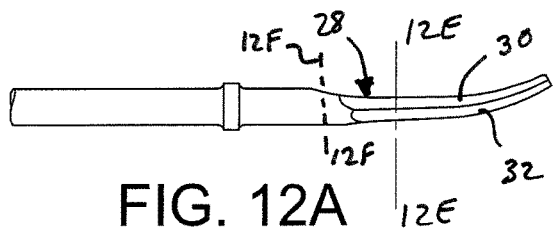
Figure 12C:
Figure 12E:
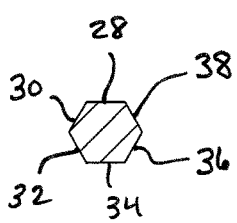
Figure 12F:
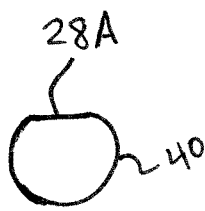
Figure 10B:
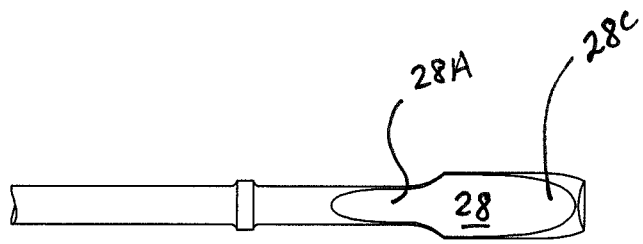
Figure 10D:
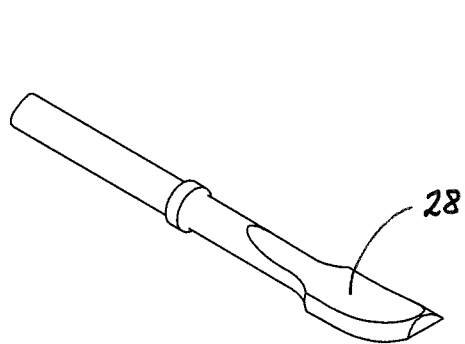
Figure 10A:
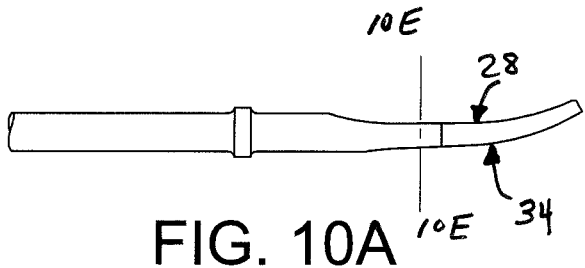
Figure 10C:
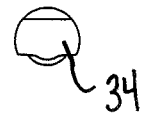
Figure 11B:
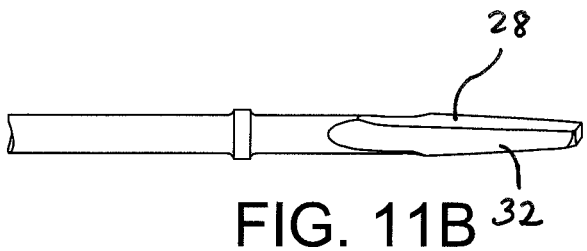
Figure 11D:
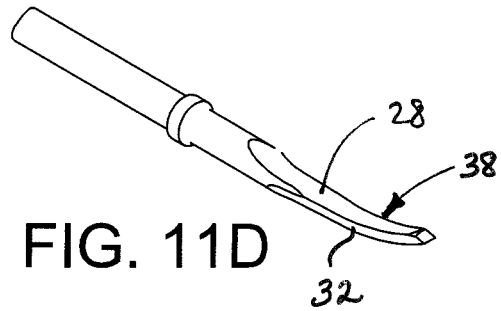
Figure 11A:
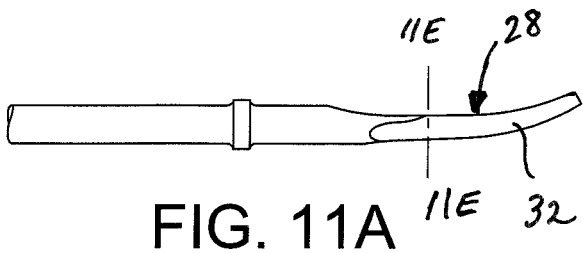
Figure 11C:
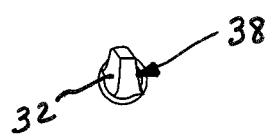

As also seen in FIGS. 4 and 5, since transition segments (A) of the faces (28-38) do not all have the same length, the cross-sectional shape of the blade in a plane perpendicular to the longitudinal axis (L) of the waveguide through some portions of transition segments (A) will include portions of a cylindrical surface (40) corresponding to that of the round stock from which the blade is fabricated (see, e.g., FIG. 12F, wherein 28A designates the transition segment of the first face (28) of the curved portion of the blade (24)). In some embodiments, transition segments A comprise less than half of the length of the curved portion of the blade, or even less than one third of the length of the curved portion of the blade.

In the alternative embodiment depicted in FIGS. 18 and 19, while the curved distal segments (C) comprise five faces, transition segments (A) include a sixth face (638A) in order to facilitate providing a reduced included angle (α) between two of the distal segment faces. Nevertheless, each face (628, 630, 632, 634, 636) includes a curved transition segment (A), a flat middle segment (B) and a curved distal segment (C). As before, transition segments (A) of each face provide a smooth transition from cylindrical portion (625) to the middle and distal segments (B, C) of the blade. Each transition segment (A) of each of the blade faces, as well as transition face (638A), is flat across its width and curves in a single direction along its length. Middle segment (B) of each of the blade faces, on the other hand, is flat across its width and also flat along its length, extending parallel to the longitudinal axis of the waveguide. Finally, distal segments (C) of each of the blade faces is flat across its width and curved (in a single direction) along its length. Also, like blade (524) in FIG. 15, first face (628) and, in part, second and fifth faces (630, 636), terminates in a cylindrical face (627).

As best seen in FIGS. 4A, 4B and 5, first face (28) intersects second face (30) along cutting edge (29), through transition segment (A), middle segment (B) and distal segment (C) of the blade (24). Similarly, second face (30) intersects third face (32) along cutting edge (31), third face (32) intersects fourth face (34) along cutting edge (33), fourth face (34) intersects fifth face (36) along cutting edge (35), fifth face (36) intersects sixth face (38) along cutting edge (37), and sixth face (38) intersects first face (28) along cutting edge (39). If desired, the cutting edges can be polished to dull the edges or ground to sharpen the edges. Polishing of the entire blade can also be performed in order to improve the surface finish, improve the life of the blade (prevent fatigue) and/or to adjust the speed of cutting. With regard to the three pairs of opposing faces of blade (24), first face (28) is in opposing relation to fourth face (34), second face (30) is in opposing relation to fifth face (36), and third face (32) is in opposing relation to sixth face (38). Since each included angle between adjacent faces is constant along the length of the curved portion of blade (24), and is about 120 degrees, the axes of curvature for the curved segments of each opposing pair of faces are parallel to one another—i.e., each pair of opposing faces only curves in the same direction (although that direction of curvature can be positive or negative). This is best seen, for example, in FIG. 5 which depicts a side plan view of blade (24) (and is the same view as FIG. 4B).

As shown in FIG. 5, transition segments (28A, 34A) of the opposing first and fourth faces (28, 34) are curved along their lengths, middle segments (28B, 34B) are flat (along their lengths and widths), and distal segments (28C, 34C) are curved along their lengths. Each of these segments (28A-C, 34A-C) is flat across its width, wherein the width extends perpendicular to the longitudinal axis (L) of the waveguide (12) (i.e., perpendicular to the plane of FIG. 5). Curved segments (28A, 28C, 34A, 34C) are all curved in the same direction, such that their axes of curvature (D', E', F', G') are parallel to each other and are perpendicular to a plane which includes the longitudinal axis (L) of the waveguide (i.e., perpendicular to the plane of FIG. 5). Of course, while the curved segments (28A, 28C, 34A, 34C) are all curved in the same direction, distal segment (34C) of fourth face (34) is negatively curved (negative radius of curvature (F)) while the other curved segments (28A, 28C, 34A) are positively curved (positive radii of curvature (D, E, F)). As used herein, a concave surface has a positive radius of curvature, while a convex surface such as distal segment (34C) of fourth face (34) has a negative radius of curvature.

In some embodiments of the blades described herein, the transition segments of each face are concave (e.g., 28A and 34A in FIG. 5). Thus, the transition segments effectively provide a taper that reduces the cross-sectional size of the blade. Also, in some embodiments of the blades described herein (e.g., blades (24, 124, 224)), when one of the middle or distal segments of each pair of opposing faces is concave (e.g., 28C in FIG. 5), the corresponding middle or distal segment of the opposing face is convex (e.g., 34C in FIG. 5). In addition, in these embodiments the radius of curvature of the concave middle or distal segment of a blade face is equal to or greater than the corresponding middle or distal segment of the opposing face. For example, in the embodiment shown in FIG. 5, the radius of curvature (E) of concave distal segment (28C) of first face (28) is greater than the radius of curvature (G) of convex distal segment (34C) of fourth face (34). In this manner, the cross-sectional area of the curved portion of the blade in these embodiments will not increase along any portion of its length. Rather, the cross-sectional area of the curved portion of the blade will decrease between its proximal and distal ends such that the blade is tapered along its length and the blade is its narrowest at distal tip (26).

Although each of the six faces (28-38) of blade (24) includes a single middle segment (28B-38B), any number of middle segments of varying curvature (or no curvature) may be provided between transition segments (28A-38A) and distal segments (28C-38C). In the embodiment shown in FIG. 5, although the middle segments of all of the faces (28-38) are not curved (i.e., have a zero curvature gradient), they are tapered such that the distance between opposing middle segments decreases in the distal direction.

It will be understood that any number of flat and curved segments may be provided on any of the plurality of faces of the curved portion of the blade. For example, in some embodiments, each face has at least one segment that is curved, such as each face having a curved distal segment, with or without distinct transition and middle segments, each of which (transition and middle segments) may be straight or curved along their length. In other embodiments the entirety of one or more faces is curved, with a single radius of curvature for the entire length of the face (e.g., first face (228) of blade (224) in FIG. 6).

Figure 20:
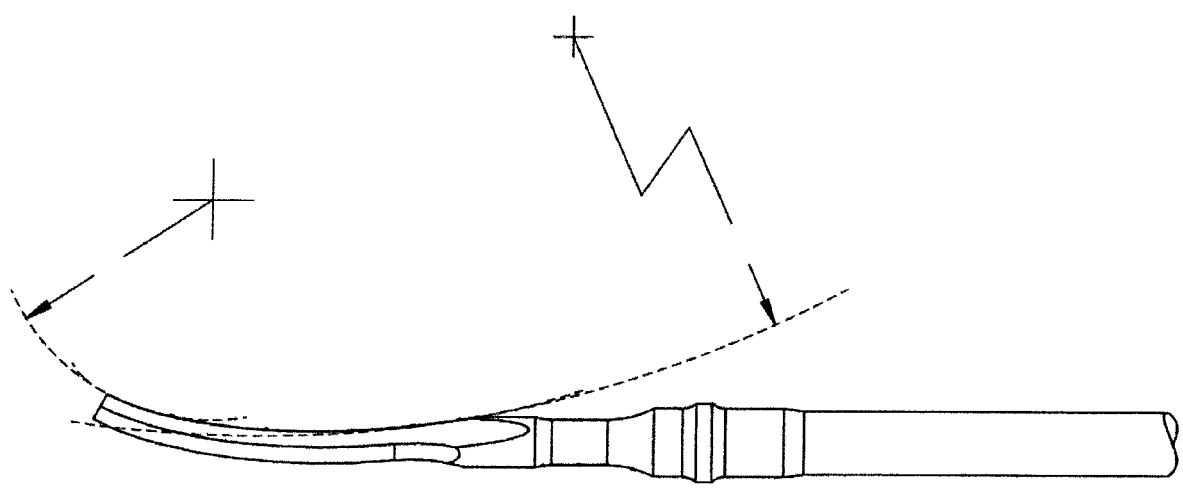
FIG. 20 is a schematic illustration of a blade having an uppermost curved face, wherein the radius of curvature of that face changes continuously along the length of that face.

FIGS. 6A-6E depict an alternative embodiment of a blade (224) having six faces (228-238) extending distally away from cylindrical portion (225) to distal tip (226). In this particular embodiment, each face (228-238) includes a transition segment (A) and a distal segment (C) (there is no flat middle segment on any of the six faces). Transition segments (A) of each face provide the transition from cylindrical portion (225) to the distal segments (C) of the blade. Like the previous embodiment, since transition segments (228A-238A) provide a taper which reduces the cross-sectional area of the blade from cylindrical portion (225) to the remainder of the curved portion of the blade, transition segments (228A-238A) gradually increase in width in the distal direction (i.e., towards distal tip (226)). Unlike blade (24), the distal end of transition segments (228A-238A) are located at varying distances from the distal end of the waveguide (212). Once again, transition segment (A) of each of the blade faces is flat across its width and curves in a single direction along its length, with each transition segment (228A-238A) being concave. Similarly, distal segment (C) of each of the blade faces is flat across its width and curved (in a single direction) along its length. In this embodiment, however, each distal segment of the blade faces comprises a complex curve of continuously changing radius, however, that curvature is nevertheless in a single direction along the length of the distal segment (e.g., as depicted schematically in FIG. 20).

As before, the six faces (228-238) of blade (224) are arranged as three pairs of opposing faces, such that the cross-sectional shape of the blade in any plane perpendicular to the longitudinal axis (L) of the waveguide through any point of distal segment (C) is a hexagon. The included angle between adjacent faces is constant along the length of the blade, and each is about 120 degrees such that the cross-sectional shape of the blade in any plane perpendicular to the longitudinal axis (L) of the waveguide through any point of distal segment (C) is an equiangular hexagon.

First face (228) intersects second face (230) along cutting edge (229), second face (230) intersects third face (232) along cutting edge (231), third face (232) intersects fourth face (234) along cutting edge (233), fourth face (234) intersects fifth face (236) along cutting edge (235), fifth face (236) intersects sixth face (238) along cutting edge (237), and sixth face (238) intersects first face (228) along cutting edge (239). With regard to the three pairs of opposing faces of blade (224), first face (228) is in opposing relation to fourth face (234), second face (230) is in opposing relation to fifth face (236), and third face (232) is in opposing relation to sixth face (238). Since each included angle between adjacent faces is constant the length of the blade (224), and about 120 degrees, the axes of curvature for the curved portions of each opposing pair of faces are parallel to one another—i.e., each pair of opposing faces only curve in the same direction (although that direction of curvature can be positive or negative, as in the previous embodiment). As with blade (24), when one distal segment (C) of a face (228-238) is concave, the distal segment (C) of the opposing face is convex (e.g., the distal segment of first face (228) is concave, and the distal segment of the opposing fourth face (234) is convex).

Figure 7:
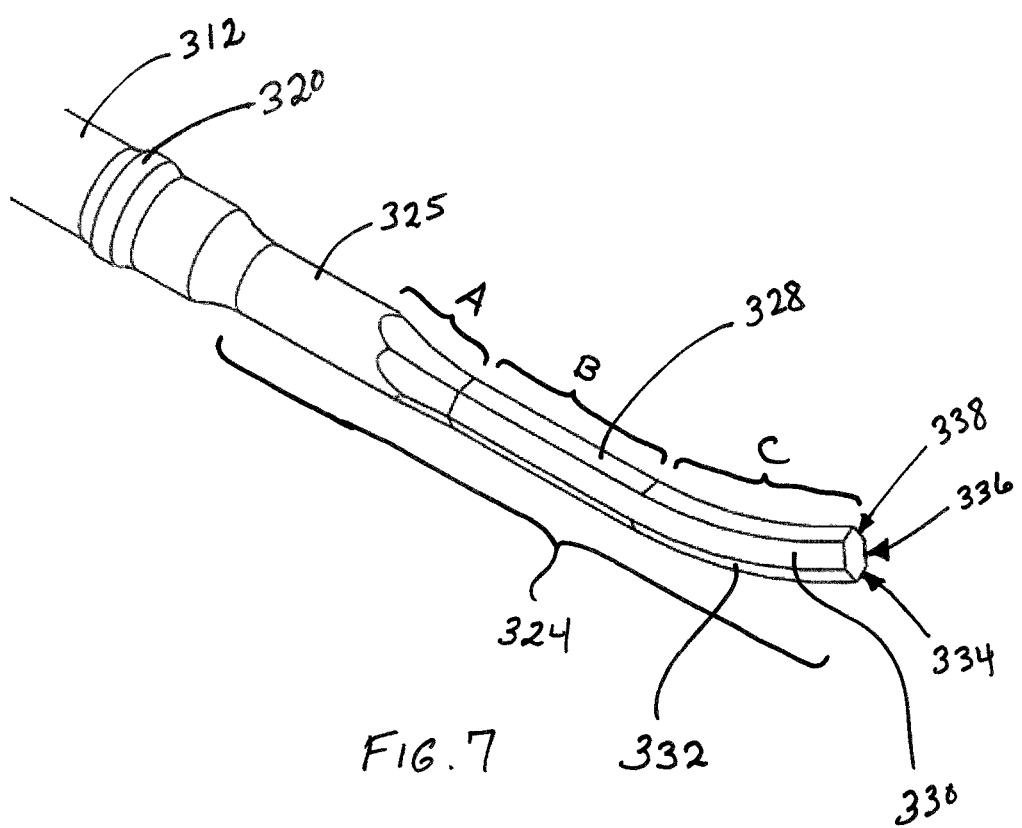
FIG. 7 depicts a perspective view of yet another embodiment of a blade.
Figure 8B:
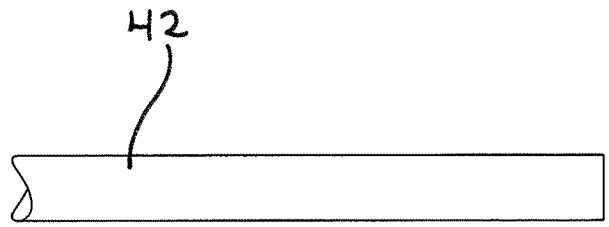
FIGS. 8-13 depict a method of manufacturing the blade of FIG. 5.
Figure 8D:
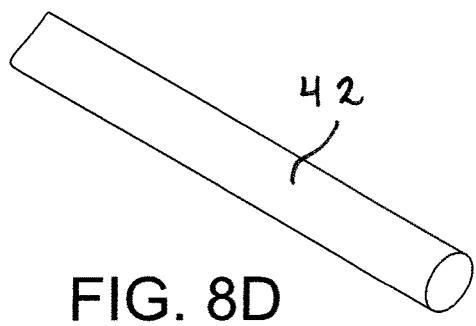
Figure 8A:
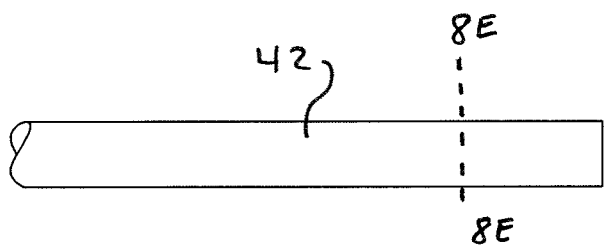
Figure 8C:
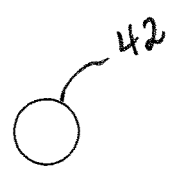
Figure 9B:
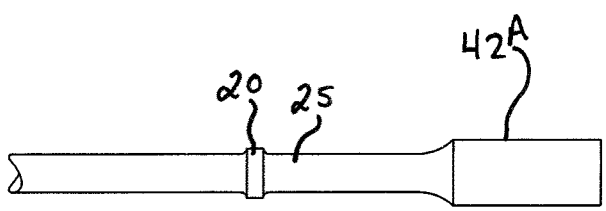
Figure 9D:
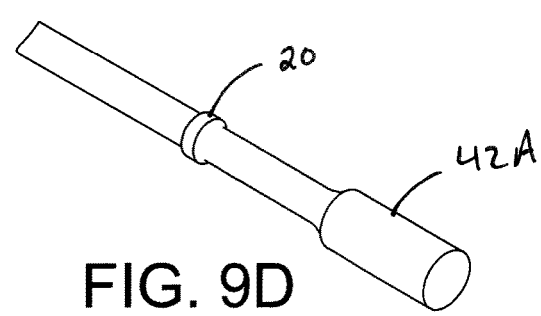
Figure 9A:
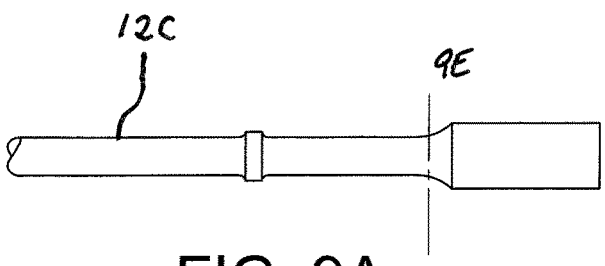
Figure 9C:
Figure 9E:
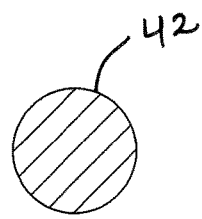
Figure 10E:
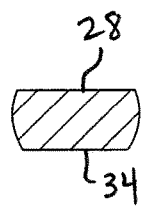
Figure 11E:
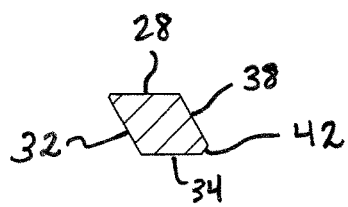

FIG. 7 depicts yet another alternative embodiment of a blade (324) having six faces (328-338) which intersect one another at included angles of about 120 degrees. Once again each face includes a transition segment (A), a middle segment (B) and a distal segment (C). As before, transition segments (328A, 330A, 332A, 334A, 336A, 338A) are flat across their respective widths and curve (concavely) in a single direction along their respective lengths. In this embodiment, however, the middle and distal segments (B, C) of opposing second and fifth faces (330, 336) are flat along their entire lengths. Faces (328, 332, 334, 338) are flat along their respective lengths at middle segments (B), but are curved in a single direction along their respective lengths at distal segments (C). Also in this embodiment, each pair of opposing faces that are curved along their distal segments (C) have the same radius of curvature such that the cross-sectional shape of the blade (324) in any plane perpendicular to the longitudinal axis (L) of the waveguide through any point of middle segment (B) or distal segment (C) is an equiangular, semi-regular hexagon (opposing sides of the hexagon are congruent, i.e., of equal length). Thus, the cross-sectional size of blade (324) does not taper apart from transition segment (A). In addition, the axis of middle segment (B) is parallel to the longitudinal axis of the waveguide.

FIGS. 8-12 depict a method of manufacturing blade (24) from a segment (42) of round stock, wherein the taper (18C) at the distal end of the waveguide (12) has been omitted from FIGS. 8-12 for purposes of clarity. The waveguide (12) and blade (24) are machined from a single round stock, and the omitted features of waveguide (12) (e.g., tapers (18)) may be formed by methods known to those skilled in the art. In particular, the diameter of segment (42) of round stock (shown in FIG. 8) has been reduced in FIG. 9 to provide not only the desired diameter of third segment (12C) of the waveguide (12), but also an annular support (20) for resilient ring (17B) which can be, for example, insert molded over the support (20) or applied over the support (20) in other ways known to those skilled in the art. Support (20) and distal cylinder (42A) can be formed, for example, by turning the round stock on a lathe to reduce its diameter, leaving distal cylinder (42A) at the end of the round stock having the same diameter as (or less than) the diameter of the original segment (42) of round stock. Distal cylinder (42A) corresponds to middle and distal segments (B, C) of the final blade (24). Alternatively, the blade faces can be milled into the full diameter round stock.

Figure 13A:
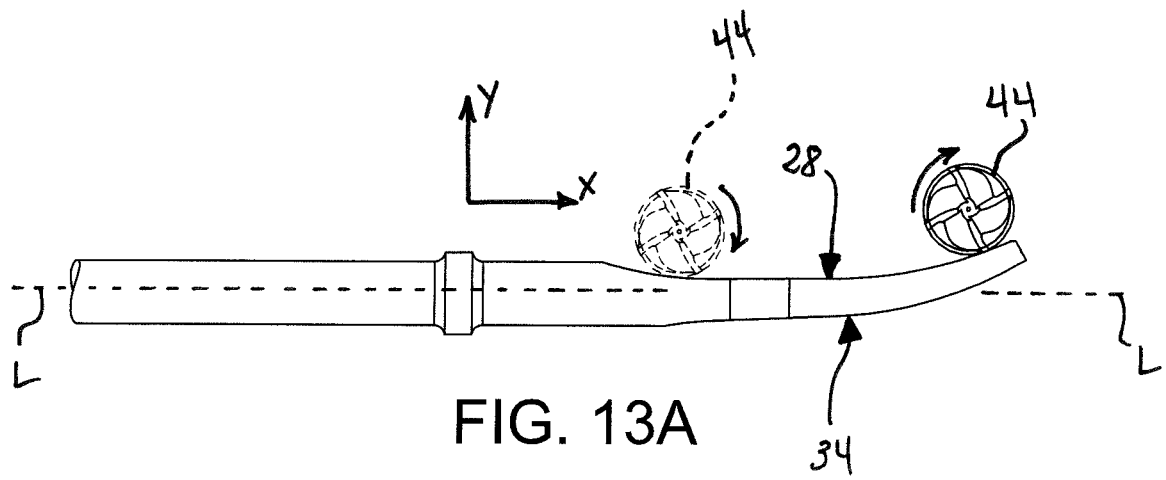
Figure 13B:
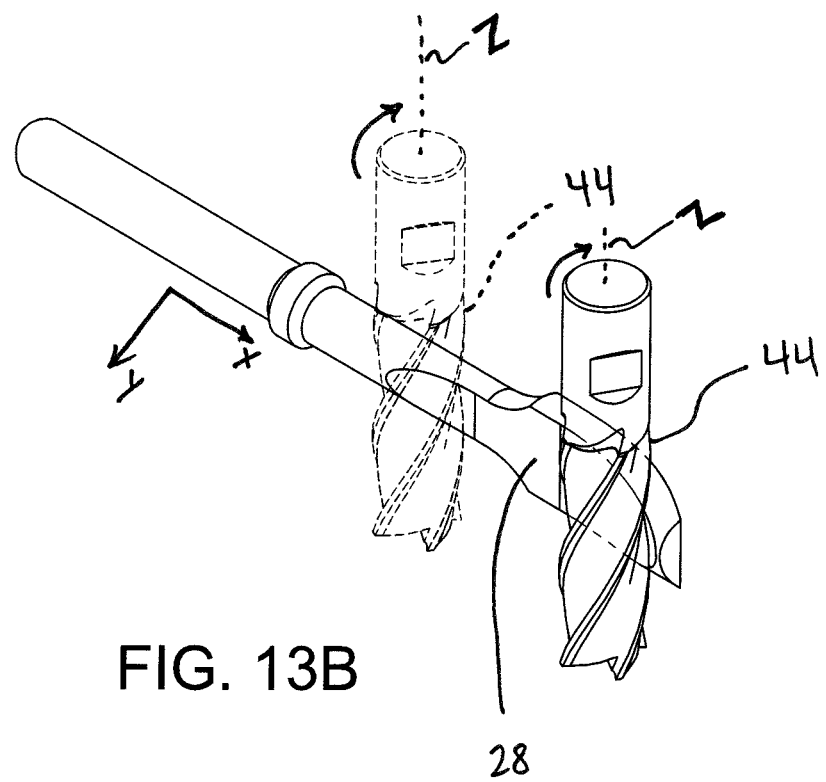

Following size reduction of the round stock to the configuration shown in FIG. 9, the six faces of the blade (24) are machined using one or more end mills to produce the configuration shown in FIG. 10. However, no Z-axis milling is required, and all six faces can be milled using just three orientations of the round stock. For example, first and fourth faces (28, 34) are milled into the round stock using an end mill (44) as shown in FIGS. 10 and 13. The workpiece (the round stock, optionally reduced in size as shown in FIGS. 9) is positioned on the X-Y table of a milling machine, as shown in FIGS. 13A and 13B. The workpiece is then advanced in the X- and Y-directions, without rotation of the workpiece, as the end mill is spinning (about a Z-oriented axis). As a result, first face (28) is milled into the workpiece, wherein first face (28) is flat across its width (i.e., the Z-direction in FIG. 13B). Fourth face (34) is milled in the same manner, without the need to rotate the workpiece about its longitudinal axis (L) but rather merely moving the workpiece in the Y-direction for reorientation prior to milling fourth face (34). (Alternatively, the workpiece may be rotated 180 degrees about its longitudinal axis from the position shown in FIG. 13 in order to machine (mill) fourth face (34).)

Next, the workpiece is rotated (clockwise, when viewed from the distal end) about its longitudinal axis (L) 60 degrees, and third and sixth faces (32, 38) are milled using one or more end mills in the same manner (i.e., only X- and Y-movement of the workpiece with respect to the end mill which is spinning about the Z-axis) (see FIG. 11). Finally, the workpiece is rotated about its longitudinal axis (L) another 60 degrees, and second and fifth faces (30, 36) are milled using one or more end mills in the same manner as before (i.e., only X- and Y-movement of the workpiece with respect to the spinning end mill) (see FIG. 12). It will be understood, of course, that the order of cutting the pairs of opposing faces may be changed. Similarly, opposing faces can be milled by moving the spinning end mill in the X- and Y-directions with respect to a stationary workpiece, or even a combination of these techniques by effecting X- and Y-movement of the workpiece with respect to a spinning end mill (i.e., by X- and Y-direction movement of both the workpiece and the spinning end mill).

Figure 14:
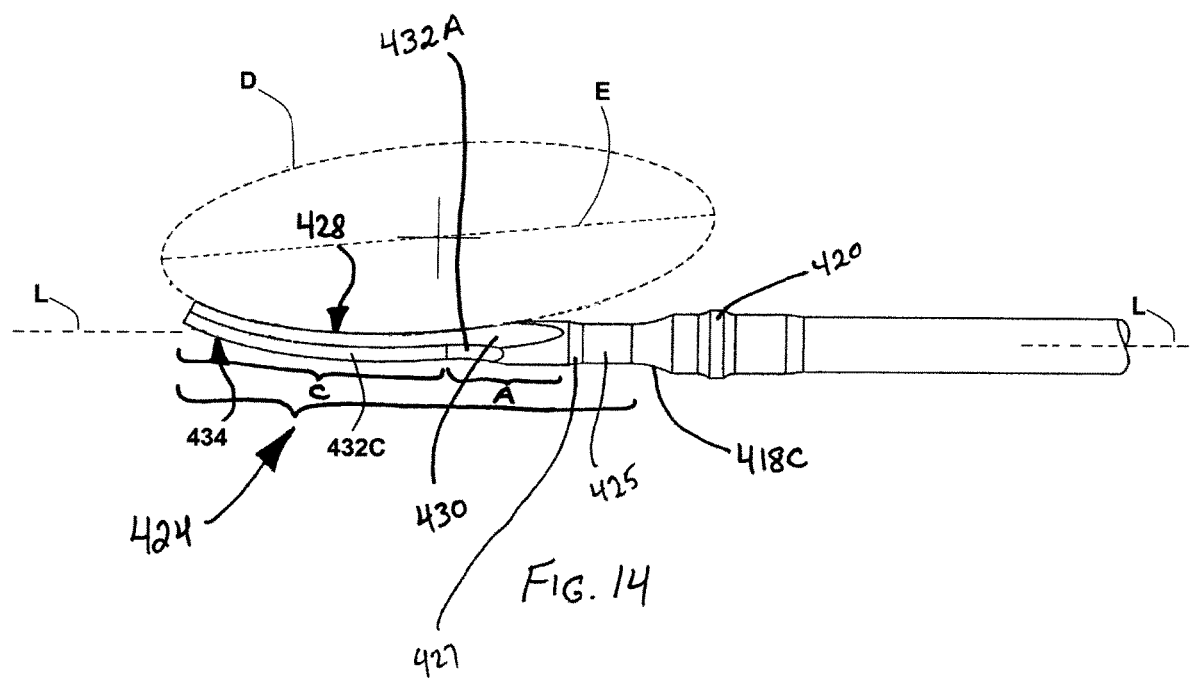
FIG. 14 depicts a side view of another alternative embodiment of a blade.

FIG. 14 depicts yet another alternative embodiment of a blade (424) having six faces which intersect at an included angle of about 120 degrees. Like the previous embodiments, each face is flat across its width and curved in a single direction along its length. In this embodiment, however, first face (428), second face (430) and the sixth face located adjacent first face (428) (not visible in FIG. 14) are continuously curved along their entire lengths, having a positive, elliptical curvature (i.e., concavely curved). As also used herein, a concave surface has a positive curvature, while a convex surface has a negative radius of curvature. As also used herein, the axis of curvature of an elliptically curved surface, such as first face (428) whose curvature is defined by an ellipse (D) in FIG. 14, is defined as a line extending through the center point of the ellipse parallel to the width of the blade face and perpendicular to the longitudinal axis (L). The axis of rotation of other complex curves can be similarly defined.

As shown in FIG. 14, along its length, the curvature of first face (428) follows a portion of an ellipse (D) that is tilted with respect to the longitudinal axis (L) of the waveguide. Thus, as seen in FIG.14, the major axis (E) of ellipse (D) is not parallel to the longitudinal axis (L), but rather is tilted at an included angle of about 5 degrees. Of course the elliptical path of first face (48) need not be tilted with respect to the longitudinal axis (L) or may be tilted to varying degrees (e.g., up to about 20 degrees, or between about 2 and about 10 degrees). Since first face (428) is continuously curved along the elliptical path its entire length, first face (428) does not include a separate and distinct transition segment. Instead, the concave transition segment is incorporated into the continuously curved first face (428). Second face (430) and the sixth face of the blade (424) are similarly elliptically curved, although not necessarily following elliptical curves identical to ellipse (D) (e.g., can be tilted or non-tilted, have different eccentricities and/or different radii). Thus, the second and sixth faces of blade (424) also do not have separate and distinct transition segments.

The distal segments (C) of the opposing faces (i.e., third face (432) in opposed relationship to the sixth face, fourth face (434) in opposed relationship to first face (428), and the fifth face in opposed relationship to second face (430)) are also elliptically curved in a similar manner, and thus comprise convexly curved elliptical surfaces. These opposing faces also have transition segments (A) (e.g., transition segment (432A) of third face (432)) which are concavely elliptically curved, as discussed previously herein. In this particular embodiment, the opposing convexly curved distal segments follow portions of tilted ellipses similar to their opposing concave faces. Thus, each pair of opposing faces are curved along their lengths in the same, singular direction, with one face of each pair concavely curved along its entire length, and the other, opposing face of each pair having a convexly curved distal segment and a concavely curved transition segment.

In addition, blade (424) is also symmetrical with respect to a plane that includes the longitudinal axis (L) of the waveguide (i.e., a plane parallel to the plane of FIG. 14 that includes longitudinal axis (L). Because of this as well as the curvature of the blade, the blade will vibrate both longitudinally and transversely (i.e., in the X- and Y-directions of FIG. 13A, but not in the Z-direction).

It will be understood, of course, that the faces of blade (424) can be curved in any of a variety of manners, such as having a single, uniform radius of curvature (i.e., a surface that follows a portion of a circular path), a constantly varying radius of curvature along its entire length (or a portion thereof), or segments of varying curved shapes and/or curvature including one more segments that are flat across both their width and length. However, the direction of curvature of each of the six faces does not change along their respective lengths, and the axes of curvature of each of pair of opposing faces (e.g., first face (428) and fourth face (434)) are parallel to one another and are perpendicular to a plane that includes the longitudinal axis (L) of the waveguide. In addition, the cross-sectional shape of blade (424) through any portion of the blade distal to the transition segments is an equiangular hexagon.

It will also be noted from FIG. 14 that, although cylindrical portion (425) extends distally away from the most-distal taper (418C) of the waveguide (located at the most-distal node of the waveguide), a distally increasing taper (427) is also provided between cylindrical portion (425) and the transition segments (A) of the blade faces.

Figure 15:
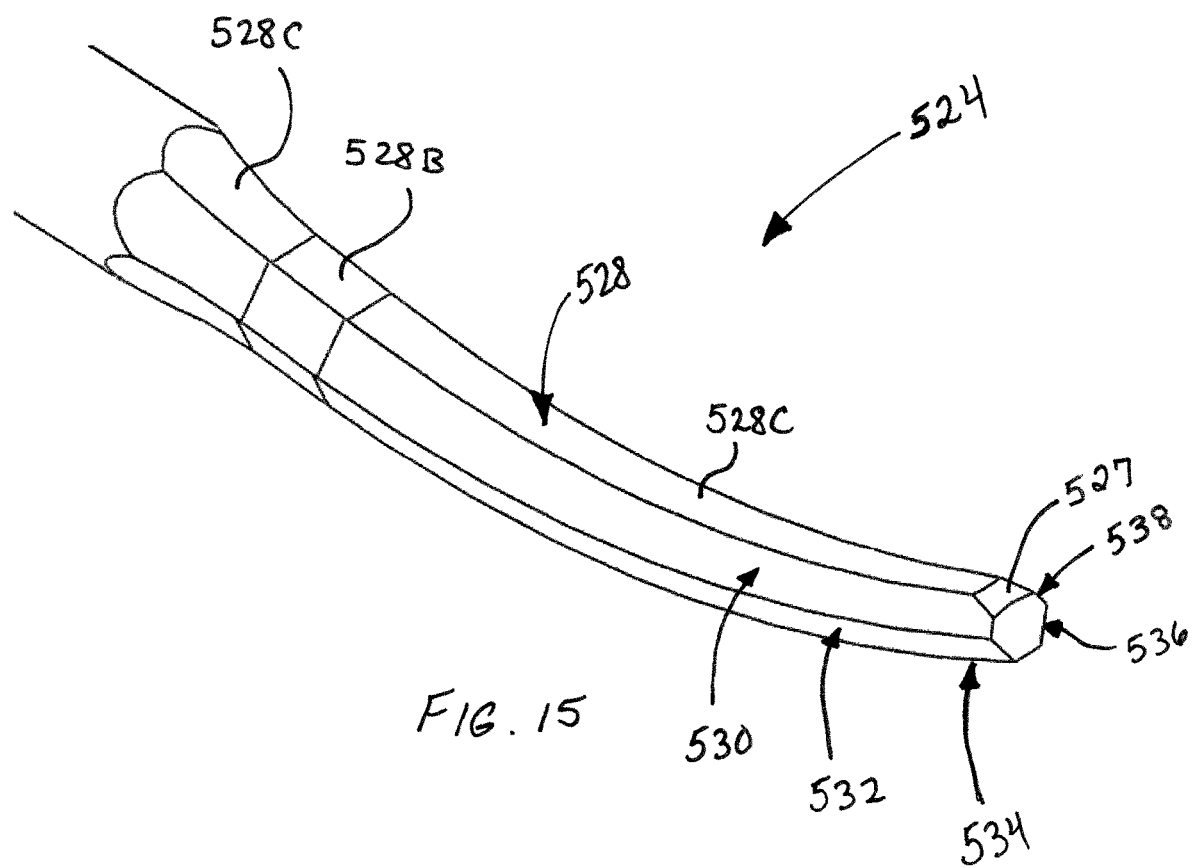
FIG. 15 depicts a perspective view of yet another embodiment of a blade.

FIG. 15 depicts yet another alternative embodiment of a blade (524) having six faces (528-538) which intersect at an included angle of about 120 degrees. Here, because the radius of curvature of distal segment (528C) of first face (528) is sufficiently small (i.e., more curvature), first face (528) ends before the distal end of the workpiece from which it has been fabricated. As a result, first face (528) and, in part, second and sixth faces (530, 538), terminates in cylindrical face (527), which is a remnant of the distal cylinder (e.g., 42A in FIG. 9) created by lathe turning of the original round stock. Thus, in the embodiment shown in FIG. 15, while the curved portion of the blade (524) once again has six faces arranged as three pairs of opposing faces, the cross-sectional shape of the blade in any plane perpendicular to the longitudinal axis of the waveguide through the curved portion of the blade is a hexagon except through the proximal-most portions of the transition segments and except through the cylindrical face (527).

FIGS. 21-25 depict another alternative embodiment of a blade (824) having six faces (828-838) which intersect at an included angle of about 120 degrees. These faces extend distally away from cylindrical portion (825) to distal tip (826). Like the previous embodiments, each face is flat across its width and curved in a single direction along its length. The six faces are arranged in three pairs, such that the cross-sectional shape of the blade in any plane perpendicular to the longitudinal axis of the waveguide through the curved portion of the blade (except through some transition segments, as described herein) is a hexagon. In addition, the opposing faces of each pair are parallel across their widths, and curve in the same direction. However, one face of a pair has a positive curvature (a concave surface) while the other face has a negative curvature (a convex surface). In addition, all of the axes of curvature of the six blade faces are perpendicular to a plane that includes the longitudinal axis (L) of the waveguide. Given the hexagonal cross-section of the blade, however, there are three such planes (one for each pair of opposed faces). Thus, the included angle between adjacent faces is a constant 120 degrees along the length of the curved portion of the blade. The intersection of each pair of adjacent faces of the curved portion of the blade defines a cutting edge for use during surgical procedures.

Figure 21:
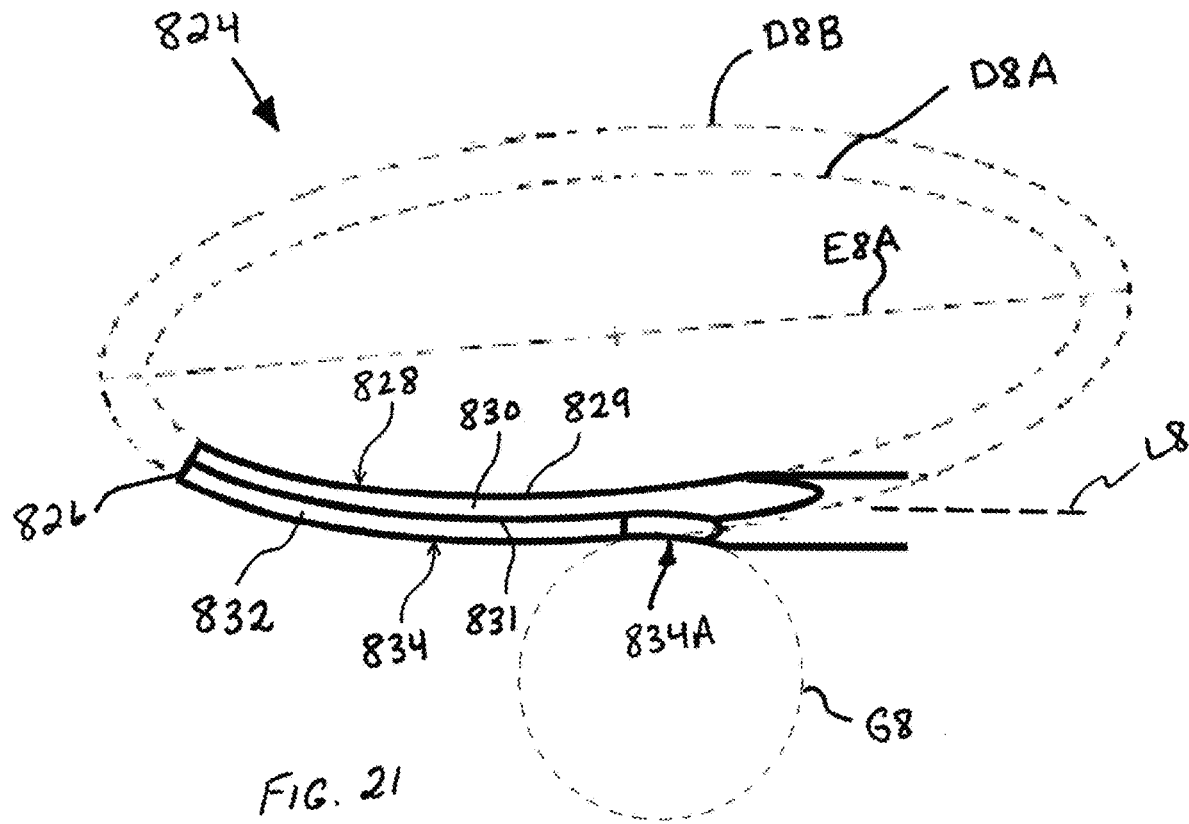
FIGS. 21-25 depict views similar to FIGS. 6B-6E of another alternative embodiment of a blade, with each successive view rotated counter-clockwise (as viewed from the distal end of the blade) from the previous view.
Figure 23:
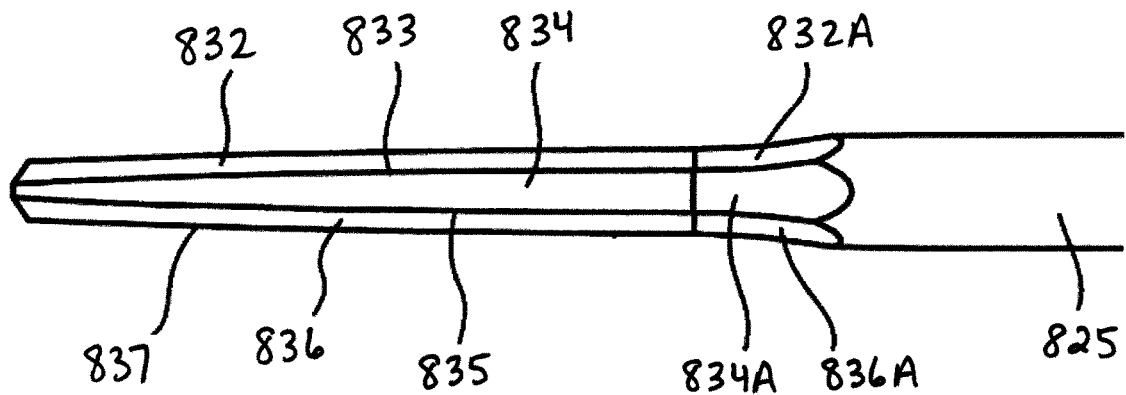
Figure 24:
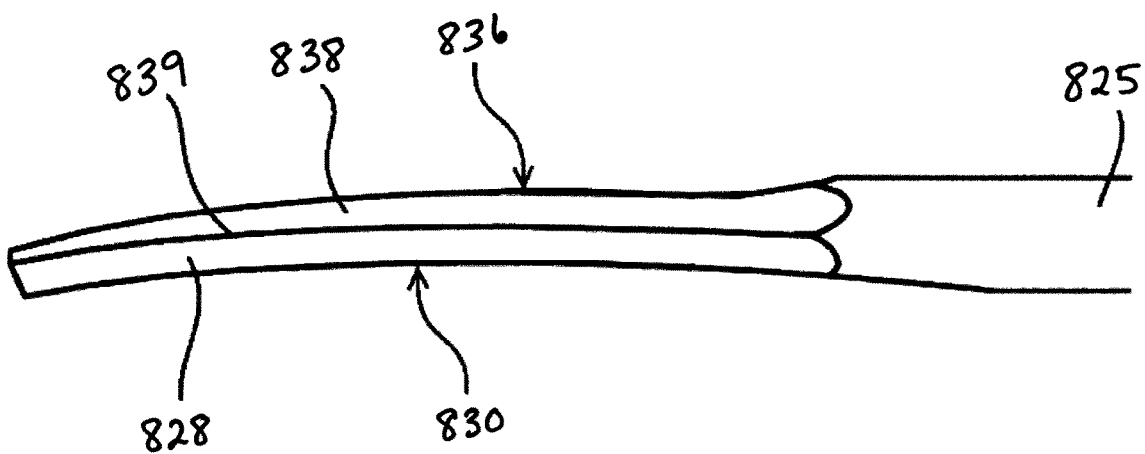

All six blade faces of blade (824) have an elliptical curvature, with the ellipses defining the curvature tilted. For the convexly curved faces, a concavely curved transition segment is once again included in order to provide a smooth transition from the cylindrical stock. The curvature of each of these transition segments follows a portion of a circle, as seen in FIGS. 21 and 23. For the three adjacent, concavely curved faces (828, 830, 838), a separate and distinct transition segment is not included, as the concave transitions from the cylindrical portion (825) are incorporated into the concavely curved face.

With reference to FIGS. 21-25, wherein each successive view is rotated counterclockwise (as viewed from the distal end of the blade), three of the faces (832, 834, 836) include a concavely curved transition segment (832A, 834A, 836A), and an elliptically curved distal portion of the face. These transition segments provide a smooth transition from the cylindrical portion to the convexly curved faces (832, 834, 836). The concavely curved faces (828, 830, 838) have no transition segments. As before, each of the transition segments of the curved blade faces is flat across its width and curves in a single direction along its length. Likewise, each distal segment of the blade faces is flat across its width and curved (in a single direction) along its length.

In the embodiment of FIGS. 21-25, first face (828), second face (830) and sixth face (838) are continuously curved along their entire lengths, having a positive, elliptical curvature (i.e., concavely curved). Thus, the first, second and sixth faces of blade (824) do not have separate and distinct transition segments. As shown in FIG. 21, along its length, the curvature of first face (828) follows a portion of an ellipse (D8A) that is tilted with respect to the longitudinal axis of the waveguide. Thus, as seen in FIG. 21, the major axis (E8A) of ellipse (D8A) is not parallel to the longitudinal axis (L9), but rather is tilted at an included angle of about 5 degrees. Of course the elliptical path of first face (848) need not be tilted with respect to the longitudinal axis (L8) or may be tilted to varying degrees (e.g., up to about 20 degrees, or between about 2 and about 10 degrees). Since first face (828) is continuously curved along this elliptical path for its entire length, first face (828) does not include a separate and distinct transition segment.

Figure 22:
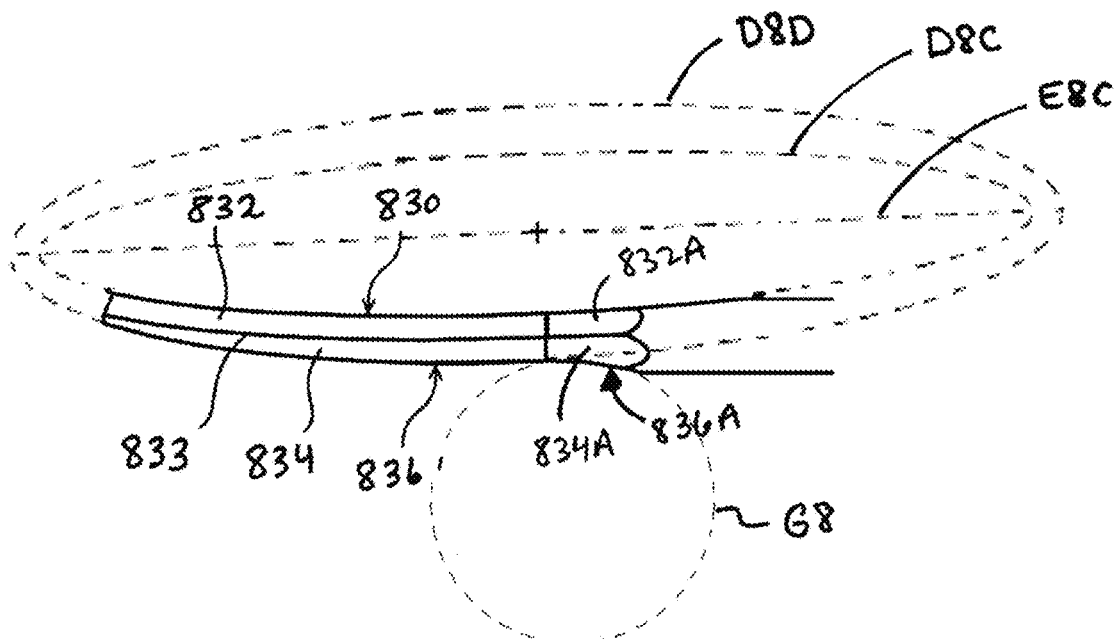

Second face (830) and sixth face (838) of the blade (824) are similarly elliptically curved, although not necessarily following elliptical curves identical to ellipse (D8A) (e.g., can be tilted or non-tilted, have different eccentricities and/or different radii). In the particular embodiment shown, the curvature of second face (830) follows a portion of an ellipse (D8C) that has a somewhat greater eccentricity than ellipse D8A. Ellipse (D8C) is once again tilted with respect to the longitudinal axis of the waveguide, as seen in FIG. 22. In this instance, the major axis (E8C) of ellipse (D8C) is tilted at an included angle of about 2.5 degrees with respect to the longitudinal axis of the waveguide. Once again the elliptical path of second face (830) need not be tilted with may be tilted to varying degrees (e.g., up to about 20 degrees, or between about 2 and about 10 degrees). Although the elliptical path of curvature of sixth face (838) is not shown in FIG. 25, the curvature of sixth face (838) follows a portion of a tilted ellipse that is similar to ellipse (D8C) shown in FIG. 22 (e.g., tilted at about 2.5 degrees, or alternatively up to about 20 degrees, or between about 2 and about 10 degrees).

The convexly curved distal portions (or segments) of the opposing faces (i.e., third face (832) in opposed relationship to the sixth face (838), fourth face (834) in opposed relationship to first face (828), and the fifth face (836) in opposed relationship to second face (830)) are also elliptically curved in a similar manner. These opposing faces also have transition segments (A) (e.g., transition segment (832A) of third face (832)) which are concavely curved, as discussed previously herein. In this particular embodiment, transition segments (832A, 834Am 836A) are flat across their widths and curve in a single direction along the length of that face. In the embodiment shown, the curvature of these transition segments (832A, 834A, 836A) follow a portion of a circle (G8) (see FIGS. 21 and 22). Once again, however, the axis of curvature of the transition segments (i.e., the center of circle (G8)) is parallel to the axis of curvature of the associated face, and is perpendicular to a plane that includes the longitudinal axis (L) of the waveguide. The transition segments may be curved along a portion of a similar circle (G8), or different sized circles can be used for one or more of the transition segments.

The opposing convexly curved distal segments of third face (832) (in opposed relationship to the sixth face (838)), fourth face (834) (in opposed relationship to first face (828)), and the fifth face (836) (in opposed relationship to second face (830)) follow portions of tilted ellipses similar to their opposing concave faces. Thus, each pair of opposing faces are curved along their lengths in the same, singular direction, with one face of each pair concavely curved along its entire length, and the other, opposing face of each pair having a convexly curved distal segment and a concavely curved transition segment.

In the specific embodiment shown, the elliptical curvature of the distal segment of fourth face (834) is not only negative (i.e., is convex), it follows a portion of an ellipse (D8B) that, like ellipse (D8A), is tilted with respect to the longitudinal axis (L) of the waveguide. In fact, although merely exemplary of one embodiment, ellipses D8A and D8B are concentric (i.e., have a common center point and major and minor axes) and have the same eccentricity. As a result, the distance between the elliptically curved portions of the first and fourth faces (828, 834) is constant along the length of the blade.

The elliptical curvature of the distal segment of fifth face (836) is also negative (i.e., is convex), following a portion of an ellipse (D8D) that is not only tilted to the same extent as ellipse (D8C), is also concentric with D8C (i.e., ellipses D8C and D8D have a common center and major and minor axes). However, the eccentricity of ellipse (D8D) is less than that of ellipse (D8C). As a result, second face (830) has slightly less curvature than fifth face (836) (i.e., is somewhat flatter), and therefore the distance between second face (830) and fifth face (836) decreases along their lengths such that the blade (824) is slightly tapered.

Figure 25:
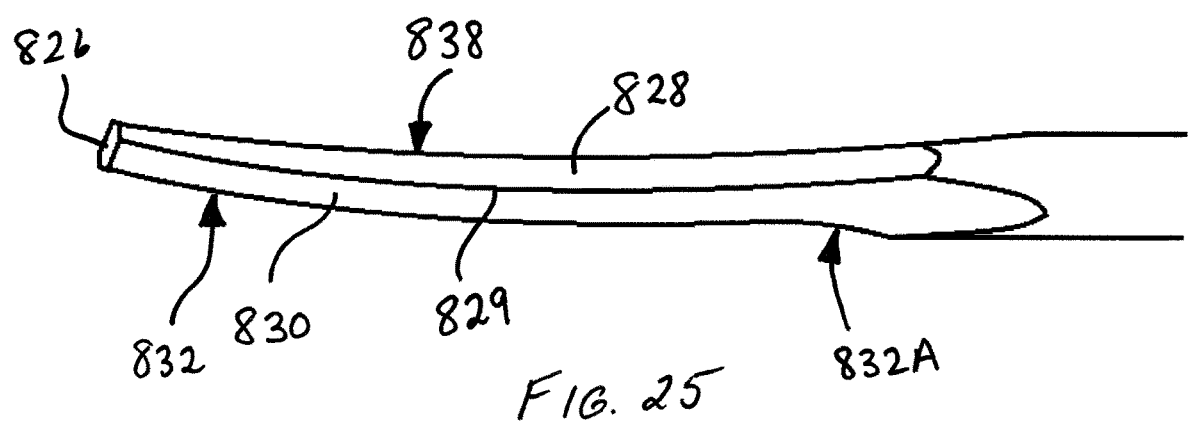

Although the elliptical path of curvature of third face (832) is not shown in FIG. 25, the curvature of third face (832) follows a portion of a tilted ellipse that is similar to ellipse (D8D) shown in FIG. 22 (e.g., tilted at about 2.5 degrees, or alternatively up to about 20 degrees, or between about 2 and about 10 degrees). Thus, the distance between third face (832) and sixth face (838) similarly decreases along their lengths, provided additional tapering of the blade (824) along its length.

In addition, blade (824) is also symmetrical with respect to a plane that includes the longitudinal axis (L) of the waveguide (i.e., a plane parallel to the plane of FIG. 21 that includes longitudinal axis (L). Because of this as well as the curvature of the blade, the blade will vibrate both longitudinally and transversely (i.e., in the X- and Y-directions of FIG. 13A, but not in the Z-direction).

It will be understood, of course, that the faces of blade (824) can be curved in any of a variety of manners, such as having a single, uniform radius of curvature (i.e., a surface that follows a portion of a circular path), a constantly varying radius of curvature along its entire length (or a portion thereof), or segments of varying curved shapes and/or curvature including one more segments that are flat across both their width and length. However, the direction of curvature of each of the six faces does not change along their respective lengths, and the axes of curvature of each of pair of opposing faces (e.g., first face (828) and fourth face (834)) are parallel to one another and are perpendicular to a plane that includes the longitudinal axis (L) of the waveguide. In addition, the cross-sectional shape of blade (824) through any portion of the blade distal to the transition segments is an equiangular hexagon.

While various embodiments of ultrasonic surgical devices and blades thereof have been described in detail above, it will be understood that the components, features and configurations, as well as the methods of manufacturing the devices and methods described herein are not limited to the specific embodiments described herein.

What is claimed is:

1. An ultrasonic surgical device comprising:
    (a) an elongate waveguide having a longitudinal axis and a distal end; and
    (b) a blade extending away from the distal end of the waveguide, said blade having a length, a distal end, and a curved portion that includes at least five faces extending lengthwise along at least a portion of the length of the blade,
    wherein each of said faces has a width that extends perpendicular to the longitudinal axis of the waveguide, a length that extends orthogonal to said width, a proximal end, and a distal end,
    wherein each of said faces is flat across its width,
    wherein each of said faces, along its length, is either flat or curved along one or more curved segments, with at least one of the faces having a convexly curved curved segment such that not all of said faces are flat along their lengths, and
    wherein each of said curved segments has an axis of curvature, wherein the axes of curvature of the one or more curved segments of an individual face are parallel to one another, and the axis of curvature of each of the curved segments of the faces of the blade is perpendicular to a plane which includes the longitudinal axis of the waveguide.

2. The ultrasonic surgical device of claim 1, wherein each pair of adjacent faces intersect along and define a cutting edge extending along at least a portion of the length of the blade, and each pair of adjacent faces defines an included angle therebetween, wherein each of said included angles is between about 100 and about 140 degrees.

3. The ultrasonic surgical device of claim 1, wherein said blade has at least six of said faces.

4. The ultrasonic surgical device of claim 3, wherein said blade has six of said faces arranged as three pairs of opposing faces, and further wherein the included angle between adjacent faces is about 120 degrees such that a cross-sectional shape of the curved portion of the blade, in any plane that extends through all six faces perpendicular to the longitudinal axis of the waveguide, is an equiangular hexagon.

5. The ultrasonic surgical device of claim 1, wherein each of said faces of the blade includes a concavely curved transition segment at its proximal end.

6. The ultrasonic surgical device of claim 1, wherein at least one of said faces has a convexly curved distal segment that extends to the distal end of the face, and another of said faces has a concavely curved distal segment that extends to the distal end of the face.

7. The ultrasonic surgical device of claim 6, wherein one or more of said faces is curved along its entire length.

8. The ultrasonic surgical device of claim 1, wherein said blade has six of said faces arranged as three pairs of opposing faces, wherein at least one of said faces has a convexly curved distal segment that extends to the distal end of the face, and the opposing face has a concavely curved distal segment that extends to the distal end of the face.

9. The ultrasonic surgical device of claim 8, each of said curved distal segments having a curvature, wherein the curvature of one of said curved distal segments is equal to or less than the curvature of the curved distal segment of the opposing face.

10. The ultrasonic surgical device of claim 9, wherein the curvature of one of said curved distal segments is less than the curvature of the curved distal segment of the opposing face such that a distal portion of the blade tapers in the distal direction.

11. The ultrasonic surgical device of claim 1, wherein each of said faces has a concavely curved transition segment at its proximal end, a flat middle segment and a distal segment that extends to the distal end of the face, at least one of said distal segments having a convex curvature and another of said distal segments having a concave curvature.

12. The ultrasonic surgical device of claim 1, wherein:
    said blade has six of said faces arranged as three pairs of opposing faces;
    the included angle between adjacent faces is about 120 degrees such that the cross-sectional shape of the blade, in any plane that extends through all six of said faces perpendicular to the longitudinal axis of the waveguide, is an equiangular hexagon; and
    a distal portion of one face of each pair of opposing faces has a positive curvature while the opposing distal portion of the other face of that pair has a negative curvature.

13. The ultrasonic surgical device of claim 12, wherein at least the distal portion of all six faces has an elliptical curvature.

14. The ultrasonic surgical device of claim 13, wherein the ellipses defining said elliptical curvatures are tilted with respect to the longitudinal axis of the waveguide.

15. The ultrasonic surgical device of claim 1, wherein said blade has six of said faces arranged as three pairs of opposing faces;

three of said faces are located adjacent to one another and are positively curved along the entire length of the face; and the other three faces are located adjacent to one another and are negatively curved along the length of a distal portion of the face, and positively curved along the length of a proximal portion of the face.

16. The ultrasonic surgical device of claim 1, wherein one or more of said faces includes a curved segment having an elliptical curvature.

17. The ultrasonic surgical device of claim 1, wherein at least one of said faces includes a curved segment having an elliptical curvature, defined by an ellipse, wherein said ellipse is tilted with respect to the longitudinal axis of the waveguide.

18. The ultrasonic surgical device of claim 1, wherein the each pair of adjacent faces intersect along and define a cutting edge extending along at least a portion of the length of the blade, wherein at least one of said cutting edges is curved in two directions along the length thereof.

19. The ultrasonic surgical device of claim 18, wherein the intersection of each pair of adjacent faces defines a curved cutting edge, wherein each of said cutting edges is curved in two directions along the length thereof.

20. The ultrasonic surgical device of claim 1, wherein each pair of adjacent faces defines an included angle therebetween, and further wherein a first one of the included angles is more than 20 degrees less than a second one of the included angles along at least a portion of the blade.

21. The ultrasonic surgical device of claim 1, wherein each of said faces extends to the distal end of said blade.

22. The ultrasonic surgical device of claim 1, wherein at least one of said faces does not extend to the distal end of said blade and terminates in a cylindrical face adjacent the distal end of the blade.

23. The ultrasonic surgical device of claim 1, wherein said waveguide and said blade are integrally formed as a unitary structure.

24. The ultrasonic surgical device of claim 1, further comprising a clamp member having a curved tissue-engaging surface, said clamp member pivotally supported adjacent the blade, wherein said tissue-engaging surface has a curvature corresponding to the curvature of at least a portion of one of the faces of the blade, and further wherein the clamp member is selectively pivotable between an open position whereat the clamp member is spaced away from the blade and a closed position whereat the clamp member can urge tissue against said one of the faces of the blade.

25. The ultrasonic surgical device of claim 1, wherein said blade has six of said faces extending lengthwise along at least portion of the length of the blade, each of said faces having a distal segment that extends to the distal end of the blade, wherein:

the faces are arranged as three pairs of opposing faces such that the opposing faces of each pair are parallel across their widths, and the axes of curvature of the one or more curved segments of the opposing faces of each pair are parallel to one another; and at least one of said distal segments has a convex curvature along its length and the distal segment of the face opposing said at least one convex distal segment has a concave curvature along its length.

26. The ultrasonic surgical instrument of claim 25, wherein each of said distal segments is curved such that the distal segment of one face of each of said pairs has a convex curvature and the distal segment of the other face of that pair has a concave curvature.

27. A method of fabricating the ultrasonic surgical device of claim 1 from a segment of round stock without Z-axis milling, comprising the step of milling said segment of round stock using an end mill in order to produce each of said faces of said blade.

* * * * *